United States Patent [19]

Schaper et al.

[11] Patent Number: 5,668,140
[45] Date of Patent: Sep. 16, 1997

[54] SUBSTITUTED 4-AMINOPYRIMIDINES, PROCESSES FOR THEIR PREPARATION, AND THEIR USE AS PESTICIDES

[75] Inventors: Wolfgang Schaper, Diedorf; Gerhard Salbeck, Kriftel; Heinz Ehrhardt, Rehling; Peter Braun, Mainz; Werner Knauf, Eppstein/Taunus; Burghard Sachse, Kelkheim; Anna Waltersdorfer, Frankfurt am Main; Manfred Kern, Lörzweiler; Peter Lümmen, Niedernhausen, all of Germany

[73] Assignee: Hoechst Aktiengesellschaft, Frankfurt, Germany

[21] Appl. No.: 461,669

[22] Filed: Jun. 5, 1995

Related U.S. Application Data

[63] Continuation of Ser. No. 883,824, May 15, 1992, abandoned.

[30] Foreign Application Priority Data

May 17, 1991 [DE] Germany ............... 41 16 089.4

[51] Int. Cl.⁶ .................. A61K 31/505; C07D 239/34; C07D 239/42
[52] U.S. Cl. .................. 514/269; 514/231.5; 514/256; 544/122; 544/123; 544/295; 544/296; 544/298; 544/326; 544/327; 544/328; 544/329
[58] Field of Search ............... 514/231.5, 256, 514/269; 544/122, 123, 295, 296, 298, 326, 327, 328, 329

[56] References Cited

U.S. PATENT DOCUMENTS

| | | | |
|---|---|---|---|
| 4,435,402 | 3/1984 | Tsuji et al. | 424/251 |
| 4,845,097 | 7/1989 | Matsumoto et al. | 514/232.2 |
| 4,895,849 | 1/1990 | Yoshioka et al. | 514/241 |
| 4,931,455 | 6/1990 | Yoshioka et al. | 514/256 |
| 4,985,426 | 1/1991 | Yoshioka et al. | 514/241 |
| 5,002,949 | 3/1991 | Peseckis et al. | 514/256 |
| 5,073,558 | 12/1991 | Obata et al. | 514/259 |

FOREIGN PATENT DOCUMENTS

| | | |
|---|---|---|
| 00057440 | 5/1985 | European Pat. Off. . |
| A 0196524 | 10/1986 | European Pat. Off. . |
| A 0264217 | 4/1988 | European Pat. Off. . |
| 0276426 | 8/1988 | European Pat. Off. . |
| A 0276406 | 8/1988 | European Pat. Off. . |
| A 0323757 | 7/1989 | European Pat. Off. . |
| A 0331529 | 9/1989 | European Pat. Off. . |
| A 0356158 | 2/1990 | European Pat. Off. . |
| 0370704 | 5/1990 | European Pat. Off. . |
| A 0453137 | 10/1991 | European Pat. Off. . |
| A 0470600 | 2/1992 | European Pat. Off. . |
| A 2363052 | 7/1974 | Germany . |
| 2043061 | 10/1980 | United Kingdom . |
| WO92/08704 | 5/1992 | WIPO . |

OTHER PUBLICATIONS

Chemical Abstracts, Band 69 (1968) 96644m.
Chemical Abstracts, Band 101 (1984) 130700t.
Chemical Abstracts, Band 101 (1984) 110939z.

*Primary Examiner*—Yogendra N. Gupta
*Attorney, Agent, or Firm*—Curtis Morris & Safford P C

[57] ABSTRACT

Substituted 4-aminopyrimidines, processes for their preparation, and their use as pesticides The invention relates to substituted 4-aminopyrimidines of the formula

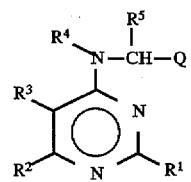

in which:

$R^1$ is hydrogen, halogen, alkyl or cycloalkyl, $R^2$ is hydrogen, alkyl, halogen, trifluoromethyl, alkoxy, haloalkoxy, alkoxyalkyl, alkylthio, alkylthioalkyl, alkylamino, dialkylamino or cycloalkylamino, $R^3$ is hydrogen, alkyl, alkoxy, haloalkoxy, alkylthio, halogen, nitro or dialkylamino, $R^4$ is hydrogen or optionally substituted carbamoyl;

$R^5$ is hydrogen, $(C_1-C_8)$alkyl or $(C_3-C_6)$cycloalkyl; and

Q has the meaning defined in the description, and their salts. The invention furthermore relates to processes for their preparation and to their use as pesticides.

20 Claims, No Drawings

SUBSTITUTED 4-AMINOPYRIMIDINES, PROCESSES FOR THEIR PREPARATION, AND THEIR USE AS PESTICIDES

This application is a continuation of application Ser. No. 07/883,824, filed May 15, 1992 now abandoned.

The invention relates to novel substituted 4-aminopyrimidines, to processes for their preparation, and to their use as pesticides, in particular as insecticide, acaricide, nematocide and fungicide.

It has already been disclosed that certain substituted 4-aminopyrimidines have a good fungicidal, acaricidal and insecticidal activity (cf. EP-OS 276,406, EP-OS 196,524, EP-OS 264,217, EP-OS 57,440, EP-OS 323,757, EP-OS 356,158, EP-OS 370,704). However, the biological activity of these compounds is not satisfactory in all fields of application, in particular when low amounts and concentrations are applied.

The invention relates to substituted 4-aminopyrimidines of the formula I

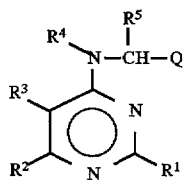

(I)

in which $R^1$ is hydrogen, halogen, $(C_1-C_4)$alkyl or $(C_3-C_6)$cycloalkyl, $R^2$ is hydrogen, $(C_1-C_4)$alkyl halogen, trifluoromethyl, $(C_1-C_4)$ alkoxy, $(C_1-C_4)$ haloalkoxy, $(C_1-C_4)$alkoxy-$(C_1-C_4)$ alkyl, $(C_1-C_4)$ alkylthio, $(C_1-C_4)$ alkylthio-$(C_1-C_4)$alkyl, $(C_1-C_4)$alkylamino, $(C_1-C_4)$ dialkylamino or $(C_3-C_6)$ cycloalkylamino, $R^3$ is hydrogen, $(C_1-C_4)$alkyl, $(C_1-C_4)$alkoxy, $(C_1-C_4)$ haloalkoxy, $(C_1-C_4)$alkylthio, halogen, nitro or $(C_1-C_4)$dialkylamino, with the proviso that, when Q is none of the groups of the meaning $Q^1$ listed below or of the formulae II', II'', II''' or II'''' and $R^3$ is a $(C_1-C_4)$ alkyl group or a halogen atom, $R^2$ is not at the same time $(C_1-C_4)$alkyl, halogen, $(C_1-C_4)$alkoxy-$(C_1-C_4)$ alkyl or $(C_1-C_4)$alkylthio-$(C_1-C_4)$alkyl, or, if Q has the meaning of $Q^1$ and $R^2$ is an ethyl group, $R^3$ is not at the same time halogen, or, if Q has the meaning of $Q^1$, $R^4$ is a radical of the formula

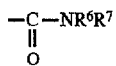

and $R^2$ is $(C_1-C_4)$alkyl or halogen, $R^3$ is not at the same time $(C_1-C_4)$alkyl or halogen, or, if Q is a radical having the meaning of $Q^1$ or of the formula II where E is a direct bond or methyleneoxy, or of the formulae II', II'', II''' or II'''', or having the meaning of $Q^3$, where $R^{14}$ is not a group having the meaning of IV, $R^2$ and $R^3$ can also together with the carbon atom to which they are bonded form an unsaturated 5-membered ring which contains an oxygen or sulfur atom bonded to the pyrimidine ring and which is optionally substituted by alkyl or halogen, $R^4$ is hydrogen or a radical

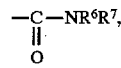

in which $R^6$ and $R^7$ are identical or different and are in each case hydrogen, $(C_1-C_4)$ alkyl, phenyl or phenyl-$(C_1-C_4)$ alkyl, where the abovementioned two phenyl groups are unsubstituted or provided with one or two substituents, it being possible for these substituents in each case to be halogen, $(C_1-C_4)$alkyl, $(C_1-C_4)$haloalkyl, $(C_1-C_4)$alkoxy, $(C_1-C_4)$-alkylthio or nitro, or $R^6$ and $R^7$ together with the nitrogen atom to which they are bonded form a saturated or unsaturated 5- or 6-membered ring which can additionally contain further nitrogen atoms or an oxygen or sulfur atom, this ring being benzo-fused and provided with one or two substituents, it being possible for these substituents in each case to be $(C_1-C_4)$alkyl, trifluoromethyl, halogen, $(C_1-C_4)$ alkoxy, $(C_1-C_4)$alkylthio or nitro, $R^5$ is hydrogen, $(C_1-C_8)$alkyl or $(C_3-C_6)$cycloalkyl, Q has the meaning of $Q^1$ and $Q^1$ is $(C_1-C_{15})$alkyl, optionally substituted by one, two or three halogen atoms, a $(C_1-C_{15})$alkoxy group, a $(C_4-C_8)$cycloalkalkoxy group, a dioxolanyl group, a $(C_1-C_4)$alkoxy-$(C_1-C_4)$alkoxy group, a hydroxyl group, a methoxycarbonyl group, a $(C_3-C_6)$cycloalkyl group, a 2-[2-(($C_1-C_4$) alkoxy)ethoxy]ethoxy group, a pyranyloxy group, an imidazol-1-yl group, a triazol-1-yl group, a pyrazol-1-yl group or a group -A-B-$R^8$ in which A is oxygen, sulfur or imino, B is carbonyl, thiocarbonyl or sulfonyl and $R^8$ is $(C_1-C_4)$alkyl, $(C_3-C_6)$cycloalkyl, $(C_1-C_4)$haloalkyl, $(C_1-C_4)$alkoxy, a substituted or unsubstituted phenoxy group, a substituted or unsubstituted phenyl group, a substituted or unsubstituted anilino group, a 2,6-dimethylmorpholin-4-yl, 4-methylpiperazin-1-yl-, imidazol-1-yl, triazol-1-yl, pyrazol-1-yl group or a mono- or di-$(C_1-C_4)$-alkylamino group, or Q has the meaning of $Q^2$ and $Q^2$ is a group of the formulae II, II', II'', II''' or II''''

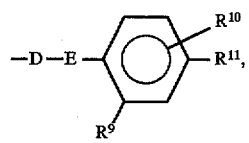   II

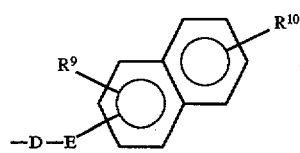   II'

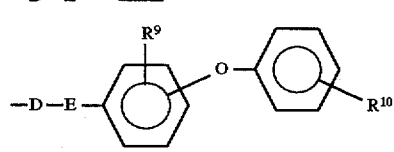   II''

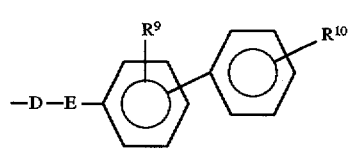   II'''

-continued

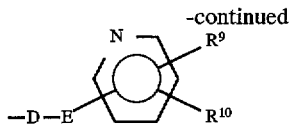

in which

D is a $(C_1-C_6)$ alkylene group,

E is a direct bond, oxygen or methyleneoxy, $R^9$ and $R^{10}$ are identical or different and in each case hydrogen, halogen, $(C_1-C_4)$ alkyl, $(C_3-C_6)$ cycloalkyl, $(C_1-C_4)$haloalkyl, $C_3$- or $C_4$-alkenyl, $(C_1-C_4)$alkoxy, $(C_1-C_4)$ alkylthio or nitro, $R^{11}$ has the meanings given for $R^9$ and $R^{10}$ and, in the event that E is oxygen, $R^{11}$ is additionally a group of the formula X-Y-(GO)$_n$-R$^{12}$ in which X is a $(C_1-C_8)$alkylene group or a $(C_1-C_8)$alkylene group having a $(C_1-C_4)$ alkoxy substituent, Y is oxygen, sulfur or an imino group, G is a $(C_1-C_8)$alkylene group or a $(C_1-C_4)$alkyleneoxy-$(C_1-C_4)$ alkylene group, n is zero or 1, $R^{12}$ is $(C_1-C_4)$alkyl, $C_3$- or $C_4$-alkenyl, $(C_4-C_6)$ alkadienyl, $C_3$- or $C_4$-alkynyl, phenyl-$(C_1-C_3)$alkyl or a group of the formula CH$_2$—W in which W is a group of the formula CH=N—OR$^{13}$ in which $R^{13}$ is hydrogen, $(C_1-C_4)$alkyl, $C_3$- or $C_4$-alkenyl or phenyl-$(C_1-C_3)$ alkyl, W is furthermore a morpholinomethyl group or a heterocyclic group having 5 to 8 ring atoms, 2 or 3 of which are oxygen or sulfur atoms, and said heterocycle is saturated or has a double bond in the ring, and said heterocycle is unsubstituted or has one or two alkyl, $(C_1-C_4)$haloalkyl or phenyl substituents, or Q has the meaning of $Q^3$ and $Q^3$ is a group of the formula III

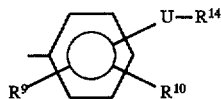

in which $R^9$ and $R^{10}$ have the meanings given above, and

U is a direct bond, oxygen, sulfur, $(C_1-C_3)$alkylene or $(C_1-C_3)$ alkyleneoxy, $R^{14}$ is phenyl or a heterocycle, it being possible for each of the abovementioned two radicals to be unsubstituted or provided with one or two substituents, where these substituents are identical or different and are in each case halogen, $(C_1-C_4)$alkyl, $(C_1-C_4)$haloalkyl, nitro, $(C_1-C_4)$alkoxy, $(C_1-C_4)$alkylthio, $(C_1-C_4)$alkoxy-$(C_1-C_4)$alkyl, phenyl, phenoxy, halophenoxy or $(C_1-C_4)$ alkylphenoxy, in the event that U is oxygen, $R^{14}$ is furthermore $(C_5-C_{10})$ alkyl, allyl, getanyl, farnesyl, $(C_1-C_4)$ haloalkyl, $(C_3-C_{10})$ cycloalkylmethyl, an ethyl group which is substituted in the 2-position by $(C_1-C_4)$alkoxy, $(C_1-C_4)$alkoxy-$(C_1-C_4)$alkyl, $(C_1-C_4)$alkylthio, $(C_1-C_4)$alkylsulfonyl or a phenoxy group which can optionally be substituted by one or two $(C_1-C_4)$ alkyl groups, or glycidyl, acetonyl, halophenoxymethyldioxolanyl, 2,2-diethoxyethyl, 1-ethoxycarbonylmethyl, trimethylsilylmethyl, 1-pyridylethyl or a $(C_1-C_4)$ alkyl group which is substituted by a $(C_1-C_4)$alkoxyimino or a benzyloxyimino group, in the event that U is oxygen, $R^{14}$ is furthermore a group of the formula IV

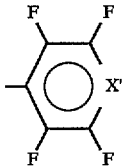

in which

X' is nitrogen or a group CR$^{15}$ in which $R^{15}$ is hydrogen, halogen, $(C_1-C_4)$alkyl, $(C_1-C_4)$ haloalkyl, $(C_1-C_4)$alkanoyl, nitro, cyano or 1,3-dioxolan-2-yl, and their salts and stereoisomers.

Preferred compounds of the formula I are those in which $R^1$ is hydrogen, methyl or halogen, $R^2$ is hydrogen, methyl, ethyl, halogen, trifluoromethyl $(C_1-C_4)$alkoxy, $(C_1-C_4)$haloalkoxy, methoxymethyl, dimethylamino or diethylamino, $R^3$ is hydrogen, $(C_1-C_4)$alkyl, $(C_1-C_4)$alkoxy, $(C_1-C_4)$ haloalkoxy or halogen, with the proviso that, when Q is none of the groups of the meaning of $Q^1$ listed below or of the formulae II', II'', II''' or II'''' and $R^3$ is a $(C_1-C_4)$alkyl group or a halogen atom, $R^2$ is not at the same time methyl, ethyl, halogen or methoxymethyl, or, if Q has the meaning of $Q^1$ and $R^2$ is an ethyl group, $R^3$ is not at the same time halogen, or, if Q has the meaning of $Q^1$, $R^4$ is a radical of the formula

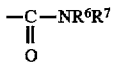

and $R^2$ is methyl, ethyl or halogen, $R^3$ is not at the same time $(C_1-C_4)$alkyl or halogen, $R^4$ is hydrogen or a radical

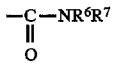

in which $R^6$ or $R^7$ are identical or different and are in each case hydrogen, $(C_1-C_4)$alkyl, phenyl or phenyl-$(C_1-C_4)$ alkyl, it being possible for the abovementioned two phenyl groups to be unsubstituted or provided with one or two substituents, where these substituents can in each case be halogen, $(C_1-C_4)$alkyl, $(C_1-C_4)$haloalkyl, $(C_1-C_4)$alkoxy, $(C_1-C_4)$alkylthio or nitro, or $R^6$ and $R^7$ together with the nitrogen atom to which they are bonded form a saturated or unsaturated 5- or 6-membered ring which can additionally contain further nitrogen atoms or an oxygen or sulfur atom, it being possible for this ring to be benzo-fused and provided with one or two substituents, where the substituents can be in each case $(C_1-C_4)$alkyl, trifluoromethyl, halogen, $(C_1-C_4)$alkoxy, $(C_1-C_4)$alkylthio or nitro, $R^5$ is hydrogen, $(C_1-C_8)$alkyl or cyclopropyl, Q has the meaning of $Q^1$ and $Q^1$ is $(C_1-C_{15})$alkyl, optionally substituted by one, two or three halogen atoms, a $(C_1-C_{15})$alkoxy group, a $(C_4-C_8)$ cycloalkylalkoxy group, a dioxolanyl group, a $(C_1-C_4)$alkoxy-$(C_1-C_4)$alkoxy group, a hydroxyl group, a methoxycarbonyl group, a $(C_3-C_6)$ cycloalkyl group, a 2-[2-(($C_1-C_4$)alkoxy)ethoxy]ethoxy group, a pyranyloxy group, an imidazol-1-yl group, a triazol-1-yl group, a pyrazol-1-yl group or a group -A-B-R$^8$ in which A is oxygen, sulfur or imino, B is carbonyl, thiocarbonyl or sulfonyl and $R^8$ is $(C_1-C_4)$alkyl, $(C_3-C_6)$cycloalkyl, $(C_1-C_4)$ haloalkyl, $(C_1-C_4)$alkoxy, a substituted or unsubstituted phenoxy group, a substituted or unsubstituted phenyl group, a substituted or unsubstituted anilino group, a 2,6-dimethylmorpholin-4-yl, 4-methylpiperazin-1-yl, imidazol-1-yl, triazol-1-yl, pyrazol-1-yl group or a mono- or di-$(C_1-C_4)$ alkylamino group, or Q has the meaning of $Q^2$ and $Q^2$ is a group of the formulae II, II', II''' or II'''' in which D is a $(C_1-C_6)$alkylene group, E is a direct bond, oxygen or methyleneoxy, $R^9$ and $R^{10}$ are identical or different and are in each case hydrogen, halogen, $(C_1-C_4)$alkyl, $(C_1-C_4)$cycloalkyl, $(C_1-C_4)$ haloalkyl, $C_3$- or $C_4$-alkenyl, $(C_1-C_4)$alkoxy, $(C_1-C_4)$alkylthio or nitro, $R^{11}$ has the meanings given for $R^9$ and $R^{10}$ and, in the event that E is oxygen, $R^{11}$ is additionally a group of the formula X-Y-(GO)$_n$-R$^{12}$ in which X is a $(C_1-C_8)$alkylene group or a $(C_1-C_4)$alkylene group having a $(C_1-C_4)$alkoxy substituent, Y is oxygen, sulfur or an imino group, G is a $(C_1-C_8)$alkylene group or a $(C_1-C_4)$alkyleneoxy-$(C_1-C_4)$alkylene group, n is zero or 1, $R^{12}$ is $(C_1-C_4)$alkyl, $C_3$- or $C_4$-alkenyl, $(C_4-C_6)$ alkadienyl, $C_3$- or $C_4$-alkynyl, phenyl-$(C_1-C_3)$alkyl or a group of the formula CH$_2$—W in which W is a group of the formula CH=N—OR$^{13}$ in which $R^{13}$ is hydrogen, $(C_1-C_4)$alkyl, $C_3$- or $C_4$-alkenyl or phenyl-$(C_1-C_3)$alkyl, W is furthermore a morpholinomethyl group or a heterocyclic group having 5 to 8 ring atoms, 2 or 3 of which are oxygen or sulfur atoms, and said heterocycle is saturated or has one double bond in the ring, and said heterocycle is unsubstituted or has one or two alkyl, $(C_1-C_4)$ haloalkyl or phenyl substituents, or Q has the meaning of $Q^3$ and $Q^3$ is a group of the formula III in which $R^9$ and $R^{10}$ have the meanings given above, U is a direct bond, oxygen, sulfur, $(C_1-C_3)$alkylene or $(C_1-C_3)$ alkyleneoxy and $R^{14}$ is phenyl or a heterocycle, it being possible for each of the abovementioned two radicals to be unsubstituted or provided with one or two substituents, where these substituents are identical or different and are in each case halogen, $(C_1-C_4)$alkyl, $(C_1-C_4)$ haloalkyl, nitro, $(C_1-C_4)$alkoxy, $(C_1-C_4)$alkylthio, $(C_1-C_4)$alkoxy-$(C_1-C_4)$ alkyl, phenyl, phenoxy, halophenoxy or $(C_1-C_4)$alkylphenoxy, in the event that U is oxygen, $R^{14}$ is furthermore $(C_5-C_{10})$alkyl, allyl, geranyl, farnesyl, $(C_1-C_4)$ haloalkyl, $(C_3-C_6)$cycloalkylmethyl, an ethyl group which is substituted in the 2-position by $(C_1-C_4)$alkoxy, $(C_1-C_4)$alkoxy-$(C_1-C_4)$alkyl, $(C_1-C_4)$ alkylthio, $(C_1-C_4)$alkylsulfonyl or a phenoxy group which can optionally be substituted by one or two $(C_1-C_4)$alkyl groups, or glycidyl, acetonyl, halophenoxymethyldioxolanyl, 2,2-diethoxyethyl, 1-ethoxycarbonylmethyl, trimethylsilylmethyl, 1-pyridylethyl or a $(C_1-C_4)$alkyl group which is substituted by a $(C_1-C_4)$alkoxyimino or a benzyloxyimino group, in the event that U is oxygen, $R^{14}$ is furthermore a group of the formula IV in which X' is nitrogen or a group CR$^{15}$ in which $R^{15}$ is hydrogen, halogen, $(C_1-C_4)$alkyl, $(C_1-C_4)$ haloalkyl, $(C_1-C_4)$alkanoyl, nitro, cyano or 1,3-dioxolan-2-yl, and their salts and stereoisomers.

More preferred are those compounds of the formula I in which $R^1$ is hydrogen, methyl or halogen, $R^2$ is hydrogen, methyl, ethyl, halogen, trifluoromethyl, $(C_1-C_4)$alkoxy, $(C_1-C_4)$haloalkoxy, methoxymethyl, dimethylamino or diethylamino, $R^3$ is hydrogen, $(C_1-C_4)$alkyl, $(C_1-C_4)$alkoxy, $(C_1-C_4)$ haloalkoxy or halogen, with the proviso that, when Q is none of the groups of the meaning of $Q^1$ listed below or of the formulae II',II'', II''' or II'''' and $R^3$ is a $(C_1-C_4)$alkyl group or a halogen atom, $R^2$ is not at the same time methyl, ethyl, halogen or methoxymethyl, or, if Q has the meaning of $Q^1$ and $R^2$ is an ethyl group, $R^3$ is not at the same time halogen, $R^4$ is hydrogen, $R^5$ is hydrogen, $(C_1-C_4)$alkyl or cyclopropyl, Q has the meaning of $Q^1$ and $Q^1$ is $(C_1-C_{15})$alkyl, optionally substituted by one, two or three halogen atoms, a $(C_1-C_{15})$alkoxy group, a $(C_4-C_8)$cycloalkylalkoxy group, a dioxolanyl group, a $(C_1-C_4)$alkoxy-$(C_1-C_4)$alkoxy group, a hydroxyl group, a methoxycarbonyl group, a $(C_3-C_6)$cycloalkyl group, a 2-[2-(($C_1-C_4$)alkoxy)ethoxy]ethoxy group, a pyranyloxy group, an imidazol-1-yl group, a triazol-1-yl group, a pyrazol-1-yl group or a group -A-B-R$^8$ in which A is oxygen, sulfur or imino, B is carbonyl, thiocarbonyl or sulfonyl, and $R^8$ is $(C_1-C_4)$alkyl, $(C_3-C_6)$cycloalkyl, $(C_1-C_4)$haloalkyl, $(C_1-C_4)$alkoxy, a substituted or unsubstituted phenoxy group, a substituted or unsubstituted phenyl group, a substituted or unsubstituted anilino group, a 2,6-di-methylmorpholin-4-yl, 4-methylpiperazin-1-yl, imidazol-1-yl, triazol-1-yl, pyrazol-1-yl group or a mono- or di-$(C_1-C_4)$ alkylamino group or $Q^1$ has the meaning of $Q^2$ and $Q^2$ is a group of the formulae II, II', II'', II''' or II'''' in which D is a $(C_1-C_6)$alkylene group, E is a direct bond, oxygen or methyleneoxy, $R^9$ and $R^{10}$ are identical or different and are in each case hydrogen, halogen, $(C_1-C_4)$alkyl, $(C_3-C_6)$cycloalkyl, $(C_1-C_4)$haloalkyl, $C_3$- or $C_4$-alkenyl, $(C_1-C_4)$alkoxy, $(C_1-C_4)$alkylthio or nitro, $R^{11}$ has the meanings given for $R^9$ and $R^{10}$ and, in the event that E is oxygen, $R^{11}$ is additionally a group of the formula X-Y-(GO)$_n$-R$^{12}$ in which X is a $(C_1-C_8)$alkylene group or a $(C_1-C_8)$alkylene group having a $(C_1-C_4)$alkoxy substituent, Y is oxygen, sulfur or an imino group, G is a $(C_1-C_8)$alkylene group or a $(C_1-C_4)$alkyleneoxy-$(C_1-C_4)$alkylene group, n is zero or 1, $R^{12}$ is $(C_1-C_4)$alkyl, $C_3$- or $C_4$-alkenyl, $(C_4-C_6)$ alkadienyl, $C_3$- or $C_4$-alkynyl, phenyl-$(C_1-C_3)$alkyl or a group of the formula CH$_2$—W in which W is a group of the formula CH=N—OR$^{13}$ in which $R^{13}$ is hydrogen, $(C_1-C_4)$alkyl, $C_3$- or $C_4$-alkenyl or phenyl-$(C_1-C_3)$alkyl, W is furthermore a morpholinomethyl group or a heterocyclic group having 5 to 8 ring atoms, 2 or 3 of which are oxygen or sulfur atoms, and said heterocycle is saturated or has a double bond in the ring and said heterocycle is unsubstituted or has one or two alkyl, $(C_1-C_4)$haloalkyl or phenyl substituents, or Q has the meaning of $Q^3$ and $Q^3$ is a group of the formula III in which $R^9$ and $R^{10}$ have the meanings given above, U is a direct bond, oxygen, sulfur, $(C_1-C_4)$alkylene or $(C_1-C_3)$alkyleneoxy, and $R^{14}$ is phenyl or a heterocycle, it being possible for each of the abovementioned two radicals to be unsubstituted or provided with one or two substituents, where these substituents are identical or different and are in each case halogen, $(C_1-C_4)$alkyl, $(C_1-C_4)$ haloalkyl, nitro, $(C_1-C_4)$alkoxy, $(C_1-C_4)$alkylthio, $(C_1-C_4)$alkoxy-$(C_1-C_4)$alkyl, phenyl, phenoxy, halophenoxy or $(C_1-C_4)$alkylphenoxy in the event that U is oxygen, $R^{14}$ is furthermore $(C_5-C_{10})$alkyl, allyl, geranyl, farnesyl, $(C_1-C_4)$ haloalkyl, $(C_3-C_6)$cycloalkylmethyl, an ethyl group which is substituted in the 2-position by $(C_1-C_4)$alkoxy, $(C_1-C_4)$alkoxy-$(C_1-C_4)$alkyl, $(C_1-C_4)$alkylthio, $(C_1-C_4)$alkylsulfonyl or a phenoxy group which can optionally be substituted by one or two $(C_1-C_4)$alkyl groups, or glycidyl, acetonyl, halophenoxymethyldioxolanyl, 2,2-diethoxyethyl, 1-ethoxycarbonylmethyl, trimethylsilylmethyl, 1-pyridylethyl or a $(C_1-C_4)$alkyl group which is substituted by a $(C_1-C_4)$alkoxyimino or a benzyloxyimino group, in the event that U is oxygen, $R^{14}$ is furthermore a group of the formula IV in which X' is nitrogen or a group $CR^{15}$ in which $R^{15}$ is hydrogen, halogen, $(C_1-C_4)$alkyl, $(C_1-C_4)$ haloalkyl, $(C_1-C_4)$alkanoyl, nitro, cyano or 1,3-dioxolan-2-yl, and their salts and stereoisomers.

Other more preferred compounds are those of the formula I in which $R^1$ is hydrogen, methyl or halogen, $R^2$ is hydrogen, methyl, ethyl, halogen, trifluoromethyl, $(C_1-C_4)$alkoxy, $(C_1-C_4)$ haloalkoxy, methoxymethyl, dimethylamino or diethylamino $R^3$ is hydrogen, $(C_1-C_4)$alkyl, $(C_1-C_4)$alkoxy, $(C_1-C_4)$ haloalkoxy or, if $R^3$ is not ethyl, $R^3$ is also halogen, $R^4$ is hydrogen, $R^5$ is hydrogen, $(C_1-C_4)$alkyl or cyclopropyl, Q has the meaning of $Q^1$ and $Q^1$ is $(C_1-C_{15})$alkyl, optionally substituted by one, two or three halogen atoms, a $(C_1-C_{15})$ alkoxy group, a $(C_4-C_8)$ cycloalkylalkoxy group, a dioxolanyl group, a $(C_1-C_4)$alkoxy-$(C_1-C_4)$alkoxy group, a hydroxyl group, a methoxycarbonyl group, a $(C_3-C_6)$cycloalkyl group, a 2-[2-(($C_1-C_4$)alkoxy)ethoxy]ethoxy group, a pyranyloxy group, an imidazol-1-yl group, a triazol-1-yl group, a pyrazol-1-yl group or a group $-A-B-R^8$ in which A is oxygen, sulfur or imino, B is carbonyl, thiocarbonyl or sulfonyl and $R^8$ is $(C_1-C_4)$alkyl, $(C_3-C_6)$cycloalkyl, $(C_1-C_4)$haloalkyl, $(C_1-C_4)$alkoxy, a substituted or unsubstituted phenoxy group, a substituted or unsubstituted phenyl group, a substituted or unsubstituted anilino group, a 2,6-dimethylmorpholin-4-yl, 4-methylpiperazin-1-yl, imidazol-1-yl, triazol-1-yl, pyrazol-1-yl group or a mono- or di-$(C_1-C_4)$ alkylamino group, and their salts and stereoisomers.

Other more preferred compounds of the formula I are those in which $R^1$ is hydrogen, methyl or halogen, $R^2$ is hydrogen, methyl, ethyl, halogen, trifluoromethyl, $(C_1-C_4)$alkoxy, $(C_1-C_4)$ haloalkoxy, methoxymethyl, dimethylamino or diethylamino, $R^3$ is hydrogen, $(C_1-C_4)$alkyl, $(C_1-C_4)$alkoxy, $(C_1-C_4)$ haloalkoxy or halogen, with the proviso that, when Q is none of the groups of the formulae II', II", II''' or II'''' listed below and $R^3$ is a $(C_1-C_4)$alkyl group or a halogen atom, $R^2$ is not at the same time methyl, ethyl, halogen or methoxymethyl, $R^4$ is hydrogen, $R^5$ is hydrogen, $(C_1-C_4)$alkyl or cyclopropyl, Q has the meaning of $Q^2$ and $Q^2$ is a group of the formulae II, II', II", II''' or II'''' in which D is a $(C_1-C_6)$alkylene group, E is a direct bond, oxygen or methyleneoxy, $R^9$ and $R^{10}$ are identical or different and are in each case hydrogen, halogen, $(C_1-C_4)$alkyl, $(C_3-C_6)$cycloalkyl, $(C_1-C_4)$ haloalkyl, $C_3$- or $C_4$-alkenyl, $(C_1-C_4)$ alkoxy, $(C_1-C_4)$ alkylthio or nitro, $R^{11}$ has the meanings given for $R^9$ and $R^{10}$ and, in the event that E is oxygen, $R^{11}$ is additionally a group of the formula X-Y-(GO)$_n$-$R^{12}$ in which X is a $(C_1-C_8)$ alkylene group or a $(C_1-C_8)$alkylene group having a $(C_1-C_4)$alkoxy substituent, Y is oxygen, sulfur or an imino group, G is a $(C_1-C_8)$alkylene group or a $(C_1-C_4)$alkyleneoxy-$(C_1-C_4)$alkylene group, n is zero or 1, $R^{12}$ is $(C_1-C_4)$ alkyl, $C_3$- or $C_4$-alkenyl, $(C_4-C_6)$ alkadienyl, $C_3$- or $C_4$-alkynyl, phenyl-$(C_1-C_3)$alkyl or a group of the formula $CH_2$—W in which W is a group of the formula $CH=N-OR^{13}$ in which $R^{13}$ is hydrogen, $(C_1-C_4)$alkyl, $C_3$- or $C_4$-alkenyl or phenyl-$(C_1-C_3)$alkyl, and W is furthermore a morpholinomethyl group or a heterocyclic group having 5 to 8 ring atoms, 2 or 3 of which are oxygen or sulfur atoms, and said heterocycle is saturated or has a double bond in the ring and said heterocycle is unsubstituted or has one or two alkyl, $(C_1-C_4)$ haloalkyl or phenyl substituents, and their salts and stereoisomers.

Other more preferred compounds of the formula I are those in which $R^1$ is hydrogen, methyl or halogen, $R^2$ is hydrogen, methyl, ethyl, halogen, trifluoromethyl, $(C_1-C_4)$alkoxy, $(C_1-C_4)$ haloalkoxy, methoxymethyl, dimethylamino or diethylamino, $R^3$ is hydrogen, $(C_1-C_4)$alkyl, $(C_1-C_4)$alkoxy, $(C_1-C_4)$ haloalkoxy or halogen, with the proviso that, if $R^3$ is $(C_1-C_4)$alkyl or halogen, $R^2$ is not at the same time halogen, methyl, ethyl or methoxymethyl, $R^4$ is hydrogen, $R^5$ is hydrogen, $(C_1-C_4)$alkyl or cyclopropyl, Q has the meaning of $Q^3$ and $Q^3$ is a group of the formula III in which $R^9$ and $R^{10}$ have the meanings mentioned, U is a direct bond, oxygen, sulfur, $(C_1-C_3)$alkylene or $(C_1-C_3)$alkyleneoxy, and $R^{14}$ is phenyl or a heterocycle, it being possible for each of the abovementioned two radicals to be unsubstituted or provided with one or two substituents, where these substituents are identical or different and are in each case halogen, $(C_1-C_4)$alkyl, $(C_1-C_4)$haloalkyl, nitro, $(C_1-C_4)$alkoxy, $(C_1-C_4)$alkylthio, $(C_1-C_4)$alkoxy-$(C_1-C_4)$alkyl, phenyl, phenoxy, halophenoxy or $(C_1-C_4)$alkylphenoxy, in the event that U is oxygen, $R^{14}$ is furthermore $(C_5-C_{10})$alkyl, allyl, geranyl, farnesyl, $(C_1-C_4)$haloalkyl, $(C_3-C_6)$cycloalkylmethyl, an ethyl group which is substituted in the 2-position by $(C_1-C_4)$alkoxy, $(C_1-C_4)$alkoxy-$(C_1-C_4)$alkyl, $(C_1-C_4)$alkylthio, a $(C_1-C_4)$alkylsulfonyl or a phenoxy group which can optionally be substituted by one or two $(C_1-C_4)$alkyl groups, or glycidyl, acetonyl, halophenoxymethyldioxolanyl, 2,2-diethoxyethyl, 1-ethoxycarbonylmethyl, trimethylsilylmethyl, 1-pyridylethyl or a $(C_1-C_4)$alkyl group which is substituted by a $(C_1-C_4)$alkoxyimino or a benzyloxyimino group, in the event that U is oxygen, $R^{14}$ is furthermore a group of the formula IV in which X' is nitrogen or a group $CR^{15}$ in which $R^{15}$ is hydrogen, halogen, $(C_1-C_4)$alkyl, $(C_1-C_4)$haloalkyl, $(C_1-C_4)$alkanoyl, nitro, cyano or 1,3-dioxolan-2-yl, and their salts and stereoisomers.

Even more preferred compounds of the formula I are those in which $R^1$ is hydrogen, methyl or halogen, $R^2$ is hydrogen, halogen, methoxy, ethoxy, trifluoromethyl, methoxymethyl, dimethylamino or diethylamino, $R^3$ is hydrogen, $(C_1-C_3)$alkyl, methoxy, ethoxy, $(C_1-C_2)$haloalkoxy or halogen, with the proviso that, when Q is none of the groups of the meaning of $Q^1$ listed below or of the formulae II', II'', II''' or II'''' and $R^3$ is a $(C_1-C_3)$alkyl group or a halogen atom, $R^2$ is not at the same time halogen or methoxymethyl, $R^4$ is hydrogen, $R^5$ is hydrogen, $(C_1-C_4)$alkyl or cyclopropyl, Q has the meaning of $Q^1$ and $Q^1$ is $(C_1-C_{15})$ alkyl, optionally substituted by one, two or three halogen atoms, a $(C_1-C_{15})$alkoxy group, a $(C_4-C_8)$ cycloalkylalkoxy group, a dioxolanyl group, a $(C_1-C_4)$alkoxy-$(C_1-C_4)$alkoxy group, a hydroxyl group, a methoxycarbonyl group, a $(C_3-C_6)$cycloalkyl group, a 2-[2-(($C_1-C_4$)alkoxy)ethoxy]ethoxy group, a pyranyloxy group, an imidazol-1-yl group, a triazol-1-yl group, a pyrazol-1-yl group or a group -A-B-$R^8$ in which A is oxygen, sulfur or imino, B is carbonyl, thiocarbonyl or sulfonyl and $R^8$ is $(C_1-C_4)$alkyl, $(C_3-C_6)$cycloalkyl, $(C_1-C_4)$haloalkyl, $(C_1-C_4)$alkoxy, a substituted or unsubstituted phenoxy group, a substituted or unsubstituted phenyl group, a substituted or unsubstituted anilino group, a 2,6-dimethylmorpholin-4-yl, 4-methylpiperazin-1-yl, imidazol-1-yl, triazol-1-yl, pyrazol-1-yl group or a mono- or di-$(C_1-C_4)$ alkylamino group, or Q has the meaning of $Q^2$ and $Q^2$ is a group of the formulae II, II', II'', II''' or II'''' in which D is a $(C_1-C_6)$alkylene group, E is a direct bond, oxygen or methyleneoxy, $R^9$ and $R^{10}$ are identical or different and are in each case hydrogen, halogen, $(C_1-C_4)$alkyl, $(C_3-C_6)$cycloalkyl, $(C_1-C_4)$haloalkyl, $C_3$- or $C_4$-alkenyl, $(C_1-C_4)$alkoxy, $(C_1-C_4)$alkylthio or nitro, $R^{11}$ has the meanings given for $R^9$ and $R^{10}$ and, in the event that E is oxygen, $R^{11}$ is additionally a group of the formula X-Y-$(GO)_n$-$R^{12}$ in which X is a $(C_1-C_8)$alkylene group or a $(C_1-C_8)$alkylene group having a $(C_1-C_4)$alkoxy substituent, Y is oxygen, sulfur or an imino group, G is a $(C_1-C_8)$ alkylene group or a $(C_1-C_4)$alkyleneoxy-$(C_1-C_4)$alkylene group, n is zero or 1, $R^{12}$ is $(C_1-C_4)$alkyl, $C_3$- or $C_4$-alkenyl, $(C_1-C_4)$ alkadienyl, $C_3$- or $C_4$-alkynyl, phenyl$(C_1-C_3)$alkyl or a group of the formula $CH_2$—W in which W is a group of the formula $CH=N$—$OR^{13}$ in which $R^{13}$ is hydrogen, $(C_1-C_4)$alkyl, $C_3$- or $C_4$-alkenyl or phenyl $(C_1-C_3)$alkyl, W is furthermore a morpholinomethyl group or a heterocyclic group having 5 to 8 ring atoms, 2 or 3 of which are oxygen or sulfur atoms, and said heterocycle is saturated or has a double bond in the ring and said heterocycle is unsubstituted or has one or two alkyl, $(C_1-C_4)$ haloalkyl or phenyl substituents, or Q has the meaning of $Q^3$ and $Q^3$ is a group of the formula III in which $R^9$ and $R^{10}$ have the meanings given above, U is a direct bond, oxygen, sulfur, $(C_1-C_3)$alkylene or $(C_1-C_3)$alkyleneoxy, and $R^{14}$ is phenyl or a heterocycle, it being possible for each of the abovementioned two radicals to be unsubstituted or provided with one or two substituents, where these substituents are identical or different and are in each case halogen, $(C_1-C_4)$alkyl, $(C_1-C_4)$haloalkyl, nitro, $(C_1-C_4)$alkoxy, $(C_1-C_4)$alkylthio, $(C_1-C_4)$alkoxy-$(C_1-C_4)$alkyl, phenyl, phenoxy, halophenoxy or $(C_1-C_4)$ alkylphenoxy, in the event that U is oxygen, $R^{14}$ is furthermore $(C_5-C_{10})$alkyl, allyl, geranyl, farnesyl, $(C_1-C_4)$haloalkyl, $(C_3-C_6)$cycloalkylmethyl, an ethyl group which is substituted in the 2-position by $(C_1-C_4)$alkoxy, $(C_1-C_4)$alkoxy-$(C_1-C_4)$alkyl, $(C_1-C_4)$ alkylthio, $(C_1-C_4)$alkylsulfonyl or a phenoxy group which can optionally be substituted by one or two $(C_1-C_4)$alkyl groups, or glycidyl, acetonyl, halophenoxymethyldioxolanyl, 2,2-diethoxyethyl, 1-ethoxycarbonylmethyl, trimethylsilylmethyl, 1-pyridylethyl or a $(C_1-C_4)$alkyl group which is substituted by a $(C_1-C_4)$alkoxyimino or a benzyloxyimino group, in the event that U is oxygen, $R^{14}$ is furthermore a group of the formula IV in which X' is nitrogen or a group $CR^{15}$ in which $R^{15}$ is hydrogen, halogen, $(C_1-C_4)$alkyl, $(C_1-C_4)$haloalkyl, $(C_1-C_4)$alkanoyl, nitro, cyano or 1,3-dioxolan-2-yl and their salts and stereoisomers.

Other even more preferred compounds of the formula I are those in which $R^1$ is hydrogen, methyl or halogen, $R^2$ is hydrogen, halogen, methoxy, ethoxy, trifluoromethyl, methoxymethyl, dimethylamino or diethylamino, $R^3$ is hydrogen, $(C_1-C_3)$alkyl, methoxy, ethoxy, $(C_1-C_2)$haloalkoxy or halogen, $R^4$ is hydrogen, $R^5$ is hydrogen, $(C_1-C_4)$alkyl or cyclopropyl, Q has the meaning of $Q^1$ and $Q^1$ is $(C_1-C_{15})$alkyl, optionally substituted by one, two or three halogen atoms, a $(C_1-C_{15})$alkoxy group, a $(C_4-C_8)$cycloalkylalkoxy group, a dioxolanyl group, a $(C_1-C_4)$alkoxy-$(C_1-C_4)$alkoxy group, a hydroxyl group, a methoxycarbonyl group, a $(C_3-C_6)$cycloalkyl group, a 2-[2-(($C_1-C_4$)alkoxy)ethoxy]ethoxy group, a pyranyloxy group, an imidazol-1-yl group, a triazol-1-yl group, a pyrazol-1-yl group or a group -A-B-$R^8$ in which A is oxygen, sulfur or imino, B is carbonyl, thiocarbonyl or sulfonyl and $R^8$ is $(C_1-C_4)$alkyl, $(C_3-C_6)$cycloalkyl, $(C_1-C_4)$haloalkyl, $(C_1-C_4)$alkoxy, a substituted or unsubstituted phenoxy group, a substituted or unsubstituted phenol group, a substituted or unsubstituted anilino group, a 2,6-dimethylmorpholin-4-yl, 4-methylpiperazin-1-yl, imidazol-1-yl, triazol-1-yl, pyrazol-1-yl group or a mono- or di-$(C_1-C_4)$ alkylamino group and their salts and stereoisomers.

Other even more preferred compounds of the formula I are those in which $R^1$ is hydrogen, methyl or halogen, $R^2$ is hydrogen, halogen, methoxy, ethoxy, trifluoromethyl, methoxymethyl, dimethylamino or diethylamino, $R^3$ is hydrogen, $(C_1-C_3)$alkyl, methoxy, ethoxy, $(C_1-C_2)$ haloalkoxy or halogen, with the proviso that, when Q is none of the groups of the formulae II, II', II'' or II''' listed below and $R^3$ is a $(C_1-C_3)$alkyl group or a halogen atom, $R^2$ is not at the same time halogen or methoxymethyl, $R^4$ is hydrogen, $R^5$ is hydrogen, $(C_1-C_4)$alkyl or cyclopropyl, Q has the meaning of $Q^2$ and $Q^2$ is a group of the formulae II, II', II'', II''' or II'''' in which D is a $(C_1-C_6)$alkylene group, E is a direct bond, oxygen or methyleneoxy, $R^9$ and $R^{10}$ are identical or different and are in each case hydrogen, halogen, $(C_1-C_4)$alkyl, $(C_3-C_6)$cycloalkyl, $(C_1-C_4)$haloalkyl, $C_3$- or $C_4$-alkenyl, $(C_1-C_4)$alkoxy, $(C_1-C_4)$alkylthio or nitro, $R^{11}$ has the meanings given for $R^9$ and $R^{10}$ and, in the event that E is oxygen, $R^{11}$ is additionally a group of the formula X-Y-(GO)$_n$-R$^{12}$ in which X is a $(C_1-C_8)$alkylene group or a $(C_1-C_8)$alkylene group having a $(C_1-C_4)$alkoxy substituent, Y is oxygen, sulfur or an imino group, G is a $(C_1-C_8)$alkylene group or a $(C_1-C_8)$alkyleneoxy $(C_1-C_4)$alkylene group, n is zero or 1, $R^{12}$ is $(C_1-C_4)$alkyl, $C_3$- or $C_4$-alkenyl, $(C_4-C_6)$ alkadienyl, $C_3$- or $C_4$-alkynyl, phenyl-$(C_1-C_3)$ alkyl or a group of the formula CH$_2$—W in which W is a group of the formula CH=N—OR$^{13}$ in which $R^{13}$ is hydrogen, $(C_1-C_4)$ alkyl, $C_3$- or $C_4$-alkenyl or phenyl-$(C_1-C_3)$alkyl, and W is furthermore a morpholinomethyl group or a heterocyclic group having 5 to 8 ring atoms, 2 or 3 of which are oxygen or sulfur atoms, and said heterocycle is saturated or has a double bond in the ring and said heterocycle is unsubstituted or has one or two alkyl, $(C_1-C_4)$ haloalkyl or phenyl substituents, and their salts and stereoisomers.

Other even more preferred compounds of the formula I are those in which $R^1$ is hydrogen, methyl or halogen, $R^2$ is hydrogen, halogen, methoxy, ethoxy, trifluoromethyl, methoxymethyl, dimethylamino or diethylamino, $R^3$ is hydrogen, $(C_1-C_3)$alkyl, methoxy, ethoxy, $(C_1-C_2)$ haloalkoxy or halogen, with the proviso that, when $R^3$ is $(C_1-C_3)$alkyl or halogen, $R^2$ is not at the same time halogen or methoxymethyl, $R^4$ is hydrogen, $R^5$ is hydrogen, $(C_1-C_4)$alkyl or cyclopropyl, Q has the meaning of $Q^3$ and $Q^3$ is a group of the formula III in which $R^9$ and $R^{10}$ have the meanings given above, U is a direct bond, oxygen, sulfur, $(C_1-C_3)$alkylene or $(C_1-C_3)$alkyleneoxy, and $R^{14}$ is phenyl or a heterocycle, it being possible for each of the abovementioned two radicals to be unsubstituted or provided with one or two substituents, where these substituents are identical or different and are in each case halogen, $(C_1-C_4)$alkyl, $(C_1-C_4)$haloalkyl, $(C_1-C_4)$ alkoxy, nitro, $(C_1-C_4)$alkylthio, $(C_1-C_4)$alkoxy-$(C_1-C_4)$alkyl, phenyl, phenoxy, halophenoxy or $(C_1-C_4)$alkylphenoxy, in the event that U is oxygen, $R^{14}$ is furthermore $(C_5-C_{10})$alkyl, allyl, geranyl, farnesyl, $(C_1-C_4)$ haloalkyl, $(C_3-C_6)$cycloalkylmethyl, an ethyl group which is substituted in the 2-position by $(C_1-C_4)$alkoxy, a $(C_1-C_4)$alkoxy-$(C_1-C_4)$alkyl, $(C_1-C_4)$alkylthio, $(C_1-C_4)$alkylsulfonyl or a phenoxy group which can optionally be substituted by one or two $(C_1-C_4)$alkyl groups, or glycidyl, acetonyl, halophenoxymethyldioxolanyl, 2,2-diethoxyethyl, 1-ethoxycarbonylmethyl, trimethylsilylmethyl, 1-pyridylethyl or a $(C_1-C_4)$alkyl group, which is substituted by a $(C_1-C_4)$alkoxyimino or a benzyloxyimino group, in the event that U is oxygen, $R^{14}$ is furthermore a group of the formula IV in which X' is nitrogen or a group CR$^{15}$ in which $R^{15}$ is hydrogen, halogen, $(C_1-C_4)$alkyl, $(C_1-C_4)$ haloalkyl, $(C_1-C_4)$alkanoyl, nitro, cyano or 1,3-dioxolan-2-yl, and their salts and stereoisomers.

Most preferred compounds of the formula I are those in which $R^1$ is hydrogen, $R^2$ is methoxy or methoxymethyl $R^3$ is methoxy, $R^4$ is hydrogen, $R^5$ is hydrogen, methyl, ethyl or cyclopropyl, Q has the meaning of $Q^1$ and $Q^1$ is $(C_1-C_{15})$alkyl, optionally substituted by one, two or three halogen atoms, a $(C_1-C_{15})$alkoxy group, a $(C_4-C_8)$cycloalkylalkoxy group, a dioxolanyl group, a $(C_1-C_4)$ alkoxy-$(C_1-C_4)$alkoxy group, a hydroxyl group, a methoxycarbonyl group, a $(C_3-C_6)$cycloalkyl group, a 2-[2-(($C_1-C_4$)alkoxy)ethoxy]ethoxy group, a pyranyloxy group, an imidazol-1-yl group, a triazol-1-yl group, a pyrazol-1-yl group or a group -A-B-R$^8$ in which A is oxygen, sulfur or imino, B is carbonyl, thiocarbonyl or sulfonyl and $R^8$ is $(C_1-C_4)$alkyl, $(C_3-C_6)$cycloalkyl, $(C_1-C_4)$haloalkyl, $(C_1-C_4)$alkoxy, a substituted or unsubstituted phenoxy group, a substituted or unsubstituted phenyl group, a substituted or unsubstituted anilino group, a 2,6-dimethylmorpholin-4-yl, 4-methylpiperazin-1-yl, imidazol-1-yl, triazol-1-yl, pyrazol-1-yl group or a mono- or di-$(C_1-C_4)$ alkylamino group, or Q has the meaning of $Q^2$ and $Q^2$ is a group of the formulae II, II', II'', II''' or II'''' in which D is a $(C_1-C_6)$alkylene group, E is a direct bond, oxygen or methyleneoxy, $R^9$ and $R^{10}$ are identical or different and are in each case hydrogen, halogen, $(C_1-C_4)$alkyl, $(C_3-C_6)$cycloalkyl, ($C_1$–$C_4$)haloalkyl, $C_3$- or $C_4$-alkenyl, ($C_1$–$C_4$)alkoxy, ($C_1$–$C_4$)alkylthio or nitro, $R^{11}$ has the meaning given for $R^9$ and $R^{10}$ and, in the event that E is oxygen, $R^{11}$ is additionally a group of the formula X-Y-(GO)$_n$-$R^{12}$ in which X is a ($C_1$–$C_4$)alkylene group or a ($C_1$–$C_8$)alkylene group having a ($C_1$–$C_4$)alkoxy substituent, Y is oxygen, sulfur or an imino group, G is a ($C_1$–$C_8$)alkylene group or a ($C_1$–$C_4$)alkyleneoxy ($C_1$–$C_4$)alkylene group, n is zero or 1, $R^{12}$ is ($C_1$–$C_4$)alkyl, $C_3$- or $C_4$-alkenyl, ($C_4$–$C_6$) alkadienyl, $C_3$- or $C_4$-alkynyl, phenyl ($C_1$–$C_3$)alkyl or a group of the formula CH$_2$—W in which W is a group of the formula CH=N—OR$^{13}$ in which $R^{13}$ is hydrogen, ($C_1$–$C_4$)alkyl, $C_3$- or $C_4$-alkenyl or phenyl-($C_1$–$C_3$) alkyl, W is furthermore a morpholinomethyl group or a heterocyclic group having 5 to 8 ring atoms, 2 or 3 of which are oxygen or sulfur atoms, and said heterocycle is saturated or has a double bond in the ring and said heterocycle is unsubstituted or has one or two alkyl, ($C_1$–$C_4$) haloalkyl or phenyl substituents, or Q has the meaning of $Q^3$ and $Q^3$ is a group of the formula III in which $R^9$ and $R^{10}$ have the meanings given above, U is a direct bond, oxygen, sulfur, ($C_1$–$C_3$)alkylene or ($C_1$–$C_3$)alkyleneoxy, and $R^{14}$ is phenyl or a heterocycle, it being possible for each of the abovementioned two radicals to be unsubstituted or provided with one or two substituents, where these substituents are identical or different and are in each case halogen, ($C_1$–$C_4$)alkyl, ($C_1$–$C_4$)haloalkyl, ($C_1$–$C_4$) alkoxy, nitro, ($C_1$–$C_4$)alkylthio, ($C_1$–$C_4$) alkoxy-($C_1$–$C_4$)alkyl, phenyl, phenoxy, halophenoxy or ($C_1$–$C_4$)alkylphenoxy, in the event that U is oxygen, $R^{14}$ is furthermore ($C_5$–$C_{10}$)alkyl, allyl, geranyl, farnesyl, ($C_1$–$C_4$) haloalkyl, ($C_3$–$C_6$)cycloalkylmethyl, an ethyl group which is substituted in the 2-position by ($C_1$–$C_4$)alkylthio, ($C_1$–$C_4$)alkylsulfonyl or a phenoxy group which can optionally be substituted by one or two ($C_1$–$C_4$)alkyl groups, or glycidyl, acetonyl, halophenoxymethyldioxolanyl, 2,2-diethoxyethyl, 1-ethoxycarbonylmethyl, trimethylsilylmethyl, 1-pyridylethyl or a ($C_1$–$C_4$)alkyl group, which is substituted by a ($C_1$–$C_4$)alkoxyimino or a benzyloxyimino group, in the event that U is oxygen, $R^{14}$ is furthermore a group of the formula IV in which X' is nitrogen or a group CR$^{15}$ in which $R^{15}$ is hydrogen, halogen, ($C_1$–$C_4$)alkyl, ($C_1$–$C_4$) haloalkyl, ($C_1$–$C_4$)alkanoyl, nitro, cyano or 1,3-dioxolan-2-yl and their salts and stereoisomers.

Other most preferred compounds of the formula I are those in which $R^1$ is hydrogen, $R^2$ is methoxymethyl $R^3$ is methoxy, $R^4$ is hydrogen, $R^5$ is hydrogen, methyl, ethyl or cyclopropyl, Q has the meaning of $Q^1$ and $Q^1$ is ($C_1$–$C_{15}$)alkyl, optionally substituted by one, two or three halogen atoms, a ($C_1$–$C_{15}$)alkoxy group, a ($C_4$–$C_8$)cycloalkylalkoxy group, a dioxolanyl group, a ($C_1$–$C_4$)alkoxy-($C_1$–$C_4$)alkoxy group, a hydroxyl group, a methoxycarbonyl group, a ($C_3$–$C_6$)cycloalkyl group, a 2-[2-(($C_1$–$C_4$)alkoxy)ethoxy]ethoxy group, a pyranyloxy group, an imidazol-1-yl group, a triazol-1-yl group, a pyrazol-1-yl group or a group -A-B-$R^8$ in which A is oxygen, sulfur or imino, B is carbonyl, thiocarbonyl or sulfonyl and $R^8$ is ($C_1$–$C_4$)alkyl, ($C_3$–$C_6$)cycloalkyl, ($C_1$–$C_4$)haloalkyl, ($C_1$–$C_4$)alkoxy, a substituted or unsubstituted phenoxy group, a substituted or unsubstituted phenyl group, a substituted or unsubstituted anilino group, a 2,6-dimethylmorpholin-4-yl, 4-methylpiperazin-1-yl, imidazol-1-yl, triazol-1-yl, pyrazol-1-yl group or a mono- or di-($C_1$–$C_4$) alkylamino group, $Q^1$ is preferably $C_3$–$C_{13}$)alkyl, or Q has the meaning of $Q^2$ and $Q^2$ is a group of the formulae II, II', II'', II''' or II'''' in which D is a ($C_1$–$C_2$)alkylene group, E is a direct bond or oxygen, $R^9$ and $R^{10}$ are identical or different and are in each case hydrogen, halogen, ($C_1$–$C_4$)alkyl, ($C_3$–$C_6$)cycloalkyl, ($C_1$–$C_4$) haloalkyl, or ($C_1$–$C_4$)alkoxy, $R^{11}$ has the meanings given for $R^9$ and $R^{10}$ and, in the event that E is oxygen, $R^{11}$ is additionally a group of the formula X-Y-(GO)$_n$-$R^{12}$ in which X is a ($C_1$–$C_2$)alkylene group, Y is oxygen, G is an ethyl group, n is zero or 1, preferably zero and $R^{12}$ is ($C_1$–$C_4$) alkyl, or Q has the meaning of $Q^3$ and $Q^3$ is a group of the formula III in which $R^9$ and $R^{10}$ have the meanings given above, and are preferably H, methyl or ethyl, U is oxygen, and $R^{14}$ is phenyl or a heterocycle, it being possible for each of the abovementioned two radicals to be unsubstituted or provided with one or two substituents, where these substituents are identical or different and are in each case halogen, ($C_1$–$C_4$)alkyl, ($C_1$–$C_4$)haloalkyl, preferably CF$_3$, ($C_1$–$C_4$)alkoxy, nitro, ($C_1$–$C_4$)alkylthio, ($C_1$–$C_4$)alkoxy-($C_1$–$C_4$)alkyl, phenyl, phenoxy, halophenoxy or ($C_1$–$C_4$)alkylphenoxy, in the event that U is oxygen, $R^{14}$ is furthermore ($C_5$–$C_{10}$)alkyl, allyl, geranyl, farnesyl, ($C_1$–$C_4$) haloalkyl or ($C_3$–$C_6$) cycloalkylmethyl, or in the event that U is oxygen, $R^{14}$ is furthermore a group of the formula IV in which X' is nitrogen or a group of the formula CF, and their salts and stereoisomers.

Other most preferred compounds of the formula I are those in which $R^1$ is hydrogen, $R^2$ is methoxy or methoxymethyl, preferably methoxymethyl, $R^3$ is methoxy, $R^4$ is hydrogen, $R^5$ is hydrogen, methyl or cyclopropyl, Q has the meaning of $Q^1$ and $Q^1$ is ($C_1$–$C_{15}$)alkyl, optionally substituted by one, two or three halogen atoms, a ($C_1$–$C_{15}$)alkoxy group, a ($C_4$–$C_8$)cycloalkylalkoxy group, a dioxolanyl group, a ($C_1$–$C_4$)alkoxy-($C_1$–$C_4$)alkoxy group, a hydroxyl group, a methoxycarbonyl group, a ($C_3$–$C_6$)cycloalkyl group, a 2-[2-(($C_1$–$C_4$)alkoxy)ethoxy]ethoxy group, a pyranyloxy group, an imidazol-1-yl group, a triazol-1-yl group, a pyrazol-1-yl group or a group -A-B-$R^8$ in which A is oxygen, sulfur or imino, B is carbonyl, thiocarbonyl or sulfonyl and $R^8$ is ($C_1$–$C_4$)alkyl, ($C_3$–$C_6$)cycloalkyl, ($C_1$–$C_4$)haloalkyl, ($C_1$–$C_4$)alkoxy, a substituted or unsubstituted phenoxy group, a substituted or unsubstituted phenyl group, a substituted or unsubstituted anilino group, a 2,6-dimethylmorpholin-4-yl, 4-methylpiperazin-1-yl, imidazol-1-yl, triazol-1-yl, pyrazol-1-yl group or a mono- or di-($C_1$–$C_4$) alkylamino group, and their salts and stereoisomers.

Other most preferred compounds of the formula I are those in which $R^1$ is hydrogen, $R^2$ is methoxy or methoxymethyl, preferably methoxymethyl, $R^3$ is methoxy, $R^4$ is hydrogen, $R^5$ is hydrogen or methyl, Q has the meaning of $Q^2$ and $Q^2$ is a group of the formulae II, II', II'', II''' or II'''' in which D is a ($C_1$- or $C_2$ )alkylene group, E is a direct bond or oxygen, $R^9$ and $R^{10}$ are identical or different and are in each case hydrogen, halogen, ($C_1$–$C_4$)alkyl, ($C_1$–$C_4$) haloalkyl, $C_3$- or $C_4$-alkenyl, ($C_1$–$C_4$)alkoxy, ($C_1$–$C_4$)alkylthio or nitro, $R^{11}$ has the meanings given for $R^9$ and $R^{10}$ and, in the event that E is oxygen, $R^{11}$ is additionally a group of the formula X-Y-(GO)$_n$-$R^{12}$ in which X is a ($C_1$–$C_8$)alkylene group or a ($C_1$–$C_8$)alkylene group having a ($C_1$–$C_4$)alkoxy substituent, Y is oxygen, sulfur or an imino group, G is a ($C_1$–$C_8$)alkylene group or a ($C_1$–$C_4$)alkyleneoxy-($C_1$–$C_4$)alkylene group, n is zero or 1, $R^{12}$ is ($C_1$–$C_4$)alkyl, $C_3$- or $C_4$-alkenyl, ($C_4$–$C_6$) alkadienyl, $C_3$- or $C_4$-alkynyl, phenyl-($C_1$–$C_3$)alkyl or a group of the formula CH$_2$—W in which W is a group of the formula CH=N—OR$^{13}$ in which $R^{13}$ is hydrogen, ($C_1$–$C_4$)alkyl, $C_3$- or $C_4$-alkenyl or phenyl-($C_1$–$C_3$)alkyl, W is furthermore a morpholinomethyl group or a heterocyclic group having 5 to 8 ring atoms, 2 or 3 of 5 which are oxygen or sulfur atoms, and said heterocycle is saturated or has a double bond in the ring and said heterocycle is unsubstituted or has one or two alkyl, ($C_1$–$C_4$) haloalkyl or phenyl substituents, and their salts and stereoisomers.

Other most preferred compounds of the formula I are those in which $R^1$ is hydrogen, $R^2$ is methoxy or methoxymethyl, preferably methoxymethyl, $R^3$ is methoxy, $R^4$ is hydrogen, $R^5$ is hydrogen, methyl, ethyl or cyclopropyl, Q has the meaning of $Q^3$ and $Q^3$ is a group of the formula III in which $R^9$ and $R^{10}$ have the meanings given above, U is a direct bond, oxygen, sulfur, ($C_1$–$C_3$)alkylene or ($C_1$–$C_3$) alkyleneoxy, and $R^{14}$ is phenyl or a heterocycle, it being possible for each of the abovementioned two radicals to be unsubstituted or provided with one or two substituents, where these substituents are identical or different and are in each case halogen, ($C_1$–$C_4$)alkyl, ($C_1$–$C_4$)haloalkyl, ($C_1$–$C_4$) alkoxy, nitro, ($C_1$–$C_4$)alkylthio, ($C_1$–$C_4$)alkoxy-($C_1$–$C_4$) alkyl, phenyl, phenoxy, halophenoxy or ($C_1$–$C_4$)alkylphenoxy, in the event that U is oxygen, $R^{14}$ is furthermore ($C_5$–$C_{10}$)alkyl, allyl, geranyl, farnesyl, ($C_1$–$C_4$)haloalkyl, ($C_3$–$C_6$)cycloalkylmethyl, an ethyl group which is substituted in the 2-position by ($C_1$–$C_4$)alkoxy, ($C_1$–$C_4$)alkoxy-($C_1$–$C_4$)alkyl, ($C_1$–$C_4$) alkylthio, ($C_1$–$C_4$)alkylsulfonyl or a phenoxy group which can optionally be substituted by one or two ($C_1$–$C_4$)alkyl groups, or glycidyl, acetonyl, halophenoxymethyldioxolanyl, 2,2-diethoxyethyl, 1-ethoxycarbonylmethyl, trimethylsilylmethyl, 1-pyridylethyl or a ($C_1$–$C_4$)alkyl group, which is substituted by a ($C_1$–$C_4$)alkoxyimino or a benzyloxyimino group, in the event that U is oxygen, $R^{14}$ is furthermore a group of the formula IV in which X' is nitrogen or a group CR$^{15}$ in which $R^{15}$ is hydrogen, halogen, ($C_1$–$C_4$)alkyl, ($C_1$–$C_4$) haloalkyl, ($C_1$–$C_4$)alkanoyl, nitro, cyano or 1,3-dioxolan-2-yl, and their salts and stereoisomers.

More preferred compounds of the formula I are also those in which $R^1$ is hydrogen, methyl or halogen, $R^2$ and $R^3$ together with the carbon atom to which they are bonded form an unsaturated 5-membered ring which contains an oxygen or sulfur atom bonded to the pyrimidine ring and which is optionally substituted by ($C_1$–$C_4$)alkyl or halogen, $R^4$ is hydrogen, $R^5$ is hydrogen, ($C_1$–$C_4$)alkyl or cyclopropyl, Q has the meaning of $Q^1$ and $Q^1$ is ($C_1$–$C_{15}$)alkyl, optionally substituted by one, two or three halogen atoms, a ($C_1$–$C_{15}$)alkoxy group, a ($C_4$–$C_8$)cycloalkylalkoxy group, a dioxolanyl group, a ($C_1$–$C_4$)alkoxy-($C_1$–$C_4$)alkoxy group, a hydroxyl group, a methoxycarbonyl group, a ($C_3$–$C_6$)cycloalkyl group, a 2-[2-(($C_1$–$C_4$)alkoxy)ethoxy]ethoxy group, a pyranyloxy group, an imidazol-1-yl group, a triazol-1-yl group, a pyrazol-1-yl group or a group -A-B-$R^8$ in which A is oxygen, sulfur or imino, B is carbonyl, thiocarbonyl or sulfonyl and $R^8$ is ($C_1$–$C_4$)alkyl, ($C_3$–$C_6$)cycloalkyl, ($C_1$–$C_4$)haloalkyl, ($C_1$–$C_4$)alkoxy, a substituted or unsubstituted phenoxy group, a substituted or unsubstituted phenyl group, a substituted or unsubstituted anilino group, a 2,6-dimethylmorpholin-4-yl, 4-methylpiperazin-1-yl, imidazol-1-yl, triazol-1-yl, pyrazol-1-yl group or a mono- or di-($C_1$–$C_4$) alkylamino group, and their salts and stereoisomers.

More preferred compounds of the formula I are also those in which $R^1$ is hydrogen, methyl or halogen, $R^2$ and $R^3$ together with the carbon atom to which they are bonded form an unsaturated 5-membered ring which contains an oxygen or sulfur atom bonded to the pyrimidine ring and which is optionally substituted by ($C_1$–$C_4$)alkyl or halogen, $R^4$ is hydrogen, $R^5$ is hydrogen, ($C_1$–$C_4$)alkyl or cyclopropyl, Q has the meaning of $Q^2$ and $Q^2$ is a group of the formulae II, II', II", II''' or II"" in which D is a $(C_1-C_6)$alkylene group, E is a direct bond or methyleneoxy, and, in the event that Q is a group of the formulae II', II", II''' or II"", E is additionally oxygen, $R^9$ and $R^{10}$ are identical or different and are in each case hydrogen, halogen, $(C_1-C_4)$alkyl, $(C_3-C_6)$cycloalkyl, $(C_1-C_4)$haloalkyl, $C_3$- or $C_4$-alkenyl, $(C_1-C_4)$alkoxy, $(C_1-C_4)$alkylthio or nitro, $R^{11}$ has the meanings given for $R^9$ and $R^{10}$, and their salts and stereoisomers.

More preferred compounds of the formula I are also those in which $R^1$ is hydrogen, methyl or halogen, $R^2$ and $R^3$ together with the carbon atom to which they are bonded form an unsaturated 5-membered ring which contains a sulfur or oxygen atom bonded to the pyrimidine ring and which is optionally substituted by $(C_1-C_4)$alkyl or halogen, $R^4$ is hydrogen, $R^5$ is hydrogen, $(C_1-C_4)$alkyl, alkyl or cyclopropyl, Q has the meaning of $Q^3$ and $Q^3$ is a group of the formula III in which $R^9$ and $R^{10}$ have the meanings given above, U is a direct bond, oxygen, sulfur, $(C_1-C_3)$alkylene or $(C_1-C_3)$alkyleneoxy, and $R^{14}$ is phenyl or a heterocycle, it being possible for each of the abovementioned two radicals to be unsubstituted or provided with one or two substituents, where these substituents are identical or different and are in each case halogen, $(C_1-C_4)$alkyl, $(C_1-C_4)$haloalkyl, $(C_1-C_4)$alkoxy, nitro, $(C_1-C_4)$alkylthio, $(C_1-C_4)$alkoxy-$(C_1-C_4)$alkyl, phenyl, phenoxy, halophenoxy or $(C_1-C_4)$alkylphenoxy, in the event that U is oxygen, R is furthermore $(C_5-C_{10})$alkyl, allyl, geranyl, farnesyl, $(C_1-C_4)$haloalkyl, $(C_3-C_6)$cycloalkylmethyl, an ethyl group which is substituted in the 2-position by $(C_1-C_4)$alkoxy, $(C_1-C_4)$alkoxy-$(C_1-C_4)$alkyl, $(C_1-C_4)$alkylthio, $(C_1-C_4)$alkylsulfonyl or a phenoxy group which can optionally be substituted by one or two $(C_1-C_4)$alkyl groups, or glycidyl, acetonyl, halophenoxymethyldioxolanyl, 2,2-diethoxyethyl, 1-ethoxycarbonylmethyl, trimethylsilylmethyl, 1-pyridylethyl or a $(C_1-C_4)$alkyl group, which is substituted by a $(C_1-C_4)$alkoxyimino or a benzyloxyimino group, and their salts and stereoisomers.

Very particularly preferred compounds of the formula I are also those in which $R^1$ is hydrogen, $R^2$ and $R^3$ together with the carbon atom to which they are bonded form an unsaturated 5-membered ring which contains a sulfur atom bonded to the pyrimidine ring, $R^4$ is hydrogen, $R^5$ is hydrogen, methyl, or cyclopropyl, Q has the meaning of $Q^1$ and $Q^1$ is $(C_1-C_{15})$alkyl, optionally substituted by one, two or three halogen atoms, a $(C_1-C_{15})$alkoxy group, a $(C_4-C_8)$cycloalkylalkoxy group, a dioxolanyl group, a $(C_1-C_4)$alkoxy-$(C_1-C_4)$alkoxy group, a hydroxyl group, a methoxycarbonyl group, a $(C_3-C_8)$cycloalkyl group, a 2-[2-(($C_1-C_4$)alkoxy)ethoxy]ethoxy group, a pyranyloxy group, an imidazol-1-yl group, a triazol-1-yl group, a pyrazol-1-yl group or a group -A-B-$R^8$ in which A is oxygen, sulfur or imino, B is carbonyl, thiocarbonyl or sulfonyl and $R^8$ is $(C_1-C_4)$alkyl, $(C_3-C_6)$cycloalkyl, $(C_1-C_4)$haloalkyl, $(C_1-C_4)$alkoxy, a substituted or unsubstituted phenoxy group, a substituted or unsubstituted phenyl group, a substituted or unsubstituted anilino group, a 2,6-dimethylmorpholin-4-yl, 4-methylpiperazin-1-yl, imidazol-1-yl, triazol-1-yl, pyrazol-1-yl group or a mono- or di-$(C_1-C_4)$ alkylamino group, and their salts and stereoisomers.

Very particularly preferred compounds of the formula I are also those in which $R^1$ is hydrogen, $R^2$ and $R^3$ together with the carbon atom to which they are bonded form an unsaturated 5-membered ring which contains a sulfur atom bonded to the pyrimidine ring, $R^4$ is hydrogen, $R^5$ is hydrogen or methyl, Q has the meaning of $Q^2$ and $Q^2$ is a group of the formulae II', II", II''' or II"" in which D is a $(C_1-C_6)$alkylene group, E is a direct bond or methyleneoxy, and, in the event that $Q^2$ is a group of the formulae II', II", II''' or II"", E is additionally oxygen, $R^9$ and $R^{10}$ are identical or different and are in each case hydrogen, halogen, $(C_1-C_4)$alkyl, $(C_3-C_6)$cycloalkyl, $(C_1-C_4)$haloalkyl, $C_3$- or $C_4$-alkenyl, $(C_1-C_4)$alkoxy, $(C_1-C_4)$alkylthio or nitro, and $R^{11}$ has the meanings given for $R^9$ and $R^{10}$ and their salts and stereoisomers.

Very particularly preferred compounds of the formula I are also those in which $R^1$ is hydrogen, $R^2$ and $R^3$ together with the carbon atom to which they are bonded form an unsaturated 5-membered ring which contains a sulfur atom bonded to the pyrimidine ring, $R^4$ is hydrogen, $R^5$ is hydrogen, methyl, ethyl or cyclopropyl, Q has the meaning of $Q^3$ and $Q^3$ is a group of the formula III in which $R^9$ and $R^{10}$ have the meanings given above, U is a direct bond, oxygen, sulfur, $(C_1-C_3)$alkylene or $(C_1-C_3)$alkyleneoxy, and $R^{14}$ is phenyl or a heterocycle, it being possible for each of the abovementioned two radicals to be unsubstituted or provided with one or two substituents, where these substituents are identical or different and are in each case halogen, $(C_1-C_4)$alkyl, $(C_1-C_4)$haloalkyl, $(C_1-C_4)$ alkoxy, nitro, $(C_1-C_4)$alkylthio, $(C_1-C_4)$ alkoxy-$(C_1-C_4)$alkyl, phenyl, phenoxy, halophenoxy or $(C_1-C_4)$alkylphenoxy, in the event that U is oxygen, $R^{14}$ is furthermore $(C_5-C_{10})$ alkyl, allyl, geranyl, farnesyl, $(C_1-C_4)$ haloalkyl, $(C_3-C_6)$cycloalkylmethyl, an ethyl group which is substituted in the 2-position by $(C_1-C_4)$alkoxy, $(C_1-C_4)$alkoxy-$(C_1-C_4)$alkyl, $(C_1-C_4)$ alkylthio, $(C_1-C_4)$alkylsulfonyl or a phenoxy group which can optionally be substituted by one or two $(C_1-C_4)$alkyl groups, or glycidyl, acetonyl, halophenoxymethyldioxolanyl, 2,2-diethoxyethyl, 1-ethoxycarbonylmethyl, trimethylsilylmethyl, 1-pyridylethyl or a $(C_1-C_4)$alkyl group, which is substituted by a $(C_1-C_4)$-alkoxyimino or a benzyloxyimino group, and their salts and stereoisomers.

In the above formula I, "halogen" is understood as meaning a fluorine, chlorine, bromine or iodine atom, preferably a chlorine or bromine atom, the term "($C_1$–$C_4$)alkyl" is understood as meaning an unbranched or branched hydrocarbon radical having 1–4 carbon atoms such as, for example, the methyl, ethyl, propyl, 1-methylethyl, 2-methylpropyl or 1,1-dimethylethyl radical, the term "($C_3$–$C_6$)cycloalkyl" is understood as meaning the cyclopropyl, cyclobutyl, cyclopentyl or cyclohexyl group, the term "($C_1$–$C_4$)alkoxy" is understood as meaning an alkoxy group whose hydrocarbon radical has the meaning given under the term "($C_1$–$C_4$)alkyl", the term "($C_1$–$C_4$)alkylthio" is understood as meaning an alkylthio group whose hydrocarbon radical has the meaning given under the term "($C_1$–$C_4$)alkyl", the term "($C_1$–$C_4$)haloalkyl" is understood as meaning one of the alkyl groups mentioned under the term "($C_1$–$C_4$) alkyl" in which one or more hydrogen atoms are replaced by the abovementioned halogen atoms, preferably chlorine or fluorine, such as, for example, the trifluoromethyl group, the 2,2,2-trifluoroethyl group, the chloromethyl or fluoromethyl group, the term "($C_1$–$C_4$)alkoxy-($C_1$–$C_4$)alkyl" is understood as meaning, for example, a 1-methoxyethyl group, a 2-methoxyethyl group, a 2-ethoxyethyl group, a methoxymethyl or ethoxymethyl group, a 3-methoxypropyl group or a 4-butoxybutyl group, the term "($C_1$–$C_4$)alkylthio-($C_1$–$C_4$)alkyl" is understood as meaning, for example, methylthiomethyl, ethylthiomethyl, propylthiomethyl, 2-methylthiomethyl, 2-ethylthioethyl or 3-methylthiopropyl, the term "($C_1$–$C_4$)alkylamino" is understood as meaning an alkylamino group whose hydrocarbon radical has the meaning given under the term "($C_1$–$C_4$)alkyl", preferably the ethylamino and methylamino group, the term "($C_1$–$C_4$)dialkylamino" is understood as meaning a dialkylamino group whose hydrocarbon radicals have the meaning given under the term "($C_1$–$C_4$)alkyl", preferably the dimethylamino and diethylamino group.

Examples of the saturated or unsaturated 5- or 6-membered ring which $R^6$ and $R^7$ together with the nitrogen atom to which they are bonded form and which can additionally contain further nitrogen atoms or an oxygen or sulfur atom are the imidazol-1-yl, the pyrazol-1-yl, 1,2,4-triazol-1-yl, the thiazol-1-yl, piperazin-1-yl, the morpholin-4-yl or thiomorpholin-4-yl group.

The term "($C_1$–$C_{15}$)alkyl" is understood as meaning a branched or unbranched hydrocarbon radical having 1–15 carbon atoms such as, for example, the radicals mentioned above under "($C_1$–$C_4$)alkyl" or the pentyl, hexyl, heptyl, octyl, 1-nonyl, 2-nonyl, 1-decyl, 2-decal, 1-undecyl, 2-undecyl, dodecyl, tridecyl, 4-methylpentyl, the tetradecyl or the pentadecyl radical, the term "($C_1$–$C_{15}$)alkoxy" is understood as meaning an alkoxy group whose alkyl groups have the meaning mentioned above under "($C_1$–$C_{15}$)alkyl", the term "($C_4$–$C_8$)-cycloalkylalkoxy" is understood as meaning, for example, the cyclopropylmethoxy group, the cyclopropylethoxy group, the cyclobutylmethoxy group, the cyclopentylmethoxy group, the cyclohexylmethoxy group or the cyclohexylethoxy group, the term "($C_1$–$C_4$)alkoxy-($C_1$–$C_4$)alkoxy" is understood as meaning, for example, a 2-ethoxyethoxy group, a 2-methoxyethoxy group, a 2-propoxyethoxy group, a 2-butoxyethoxy group, a 3-methoxypropoxy group or a 4-methoxybutoxy group, the term "($C_1$–$C_6$)alkylene" is understood as meaning a straight-chain or branched alkylene chain having 1–6 carbon atoms such as, for example, the methylene group, the ethylene group, the trimethylene group, the tetramethylene group, —CH($CH_3$)—,

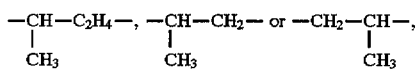

the term "($C_1$–$C_8$)alkylene" is understood as meaning a straight-chain or branched alkylene chain having 1–8 carbon atoms such as, for example, the radicals mentioned above under "($C_1$–$C_3$)alkylene" or the tetramethylene group, the pentamethylene group, the hexamethylene group, the heptamethylene group or the octamethylene group, the term "$C_3$- or $C_4$-alkenyl" is understood as meaning allyl, 1-methylallyl, 2-methylallyl, 1-butenyl or 2-butenyl, the term "($C_4$–$C_6$)alkadienyl" is understood as meaning 1,3-butadienyl or 1,4-hexadienyl, the term "$C_3$- or $C_4$-alkynyl" is understood as meaning 1-propynyl, 2-propynyl or 2-butynyl, and the term "phenyl-($C_1$–$C_3$)alkyl" is understood as meaning, for example, benzyl, phenylethyl or α-methylbenzyl.

The explanation given above applies analogously to homologs.

The present invention relates to the compounds of the formula I in the form of the free base or in the form of an acid addition salt. Acids which can be used for salt formation are inorganic acids such as hydrochloric acid, hydrobromic acid, nitric acid, sulfuric acid, phosphoric acid, or organic acids such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

Some of the compounds of the formula I have one or more asymmetric carbon atoms. Racemates and diastereomers can therefore occur. The invention embraces the pure isomers as well as their mixtures. The mixtures of diastereomers can be resolved to give the components by customary methods, for example by selective crystallization from suitable solvents or by chromatography. Racemates can be resolved into the enantiomers by conventional methods, for example by salt formation with an optically active acid, separation of the diastereomeric salts and setting free of the pure enantiomers by means of a base.

The invention furthermore relates to a process for the preparation of compounds of the formula I, which comprises reacting a compound of the formula V

in which $R^1$, $R^2$ and $R^3$ have the meanings given under formula I and Z is the leaving group halogen, alkylthio, alkanesulfonyloxy or arylsulfonyloxy, alkylsulfonyl or arylsulfonyl, with an amine of the formula VI,

in which $R^5$ and Q have the meanings given under formula I, and, if appropriate, carbamoylating the resulting compounds of the formula I on the nitrogen or chlorinating or brominating them on the $C_5$ atom of the pyrimidine.

The above-described substitution reaction is known in principle. The leaving group Z can be varied within wide limits and can be, for example, a halogen atom such as fluorine, chlorine, bromine or iodine, or alkylthio such as methylthio or ethylthio, or alkanesulfonyloxy such as methane-, trifluoromethane- or ethanesulfonyloxy, or arylsulfonyloxy such as benzenesulfonyloxy or toluenesulfonyloxy, or alkylsulfonyl such as methyl- or ethylsulfonyl, or arylsulfonyl such as phenyl- or toluenesulfonyl.

The abovementioned reaction is carried out in a temperature range from 20°–150° C., expediently in the presence of a base and, if appropriate, in an inert organic solvent such as N,N-dimethylformamide, N,N-dimethylacetamide, dimethylsulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the solvents mentioned can also be used.

Examples of suitable bases are carbonates, hydrogen carbonates, hydroxides, alcoholates or hydrides of alkali metals or alkaline earth metals, such as sodium carbonate, sodium hydrogen carbonate, potassium carbonate, sodium hydroxide, sodium methylate or sodium hydride, or organic bases such as triethylamine or pyridine. A second equivalent of the amine VI can also be employed as auxiliary base.

The invention furthermore relates to a process for the preparation of compounds of the formula I'

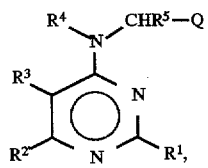

in which $R^1$, $R^3$, $R^4$, $R^5$ and Q have the meanings given under the formula I and $R^{2'}$ is $(C_1-C_4)$alkoxy, $(C_1-C_4)$haloalkoxy, $(C_1-C_4)$alkylthio, $(C_1-C_4)$alkylamino or $(C_1-C_4)$ dialkylamino, which comprises reacting a compound of the formula VII

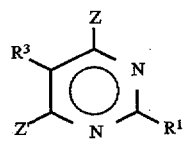

in which Z and Z' can be identical or different and the leaving group is halogen, alkylthio, alkanesulfonyloxy, arylsulfonyloxy, alkylsulfonyl or arylsulfonyl, and $R^1$ and $R^3$ have the meaning given under formula I, with a compound of the formula VI

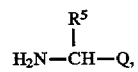

in which $R^5$ and Q have the meanings given under formula I, to give a compound of the formula VIII

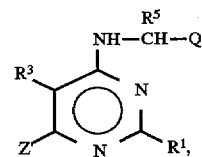

in which $R^1$, $R^3$, $R^5$, Q and Z' have the meanings given above, and, in a second reaction step reacting the compound of the formula VIII with a compound of the formula IX $$HR^{2'} \quad (IX),$$

in which $R^{2'}$ has the meanings given above, and, if appropriate, carbamoylating the resulting compound of the formula I' on the nitrogen or, if appropriate and if $R^3$ is hydrogen, chlorinating or brominating the compound.

The procedure for the preparation of the compounds of the formula I' is completely analogous to the above-described preparation of the compounds of the formula I by reacting the compounds V with the compounds VI.

The leaving group Z' required in the second reaction step can have the same meaning as the above-described leaving group Z. As regards the reaction conditions, the same solvents, auxiliary bases and reaction temperatures can be used in the second reaction step as in the above-described preparation of the compounds of the formula I from the compounds of the formulae V and VI. Both reaction steps can be carried out without working-up after the first reaction step in the form of a one-pot reaction.

The invention furthermore relates to a process for the preparation of compounds of the formula I', which comprises reacting a compound of the abovementioned formula VII with a compound of the formula IX to give a compound of the formula X

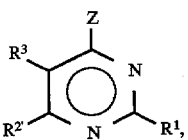

in which $R^1$ and $R^3$ have the meaning given under formula I, $R^{2'}$ is $(C_1-C_4)$alkoxy, $(C_1-C_4)$haloalkoxy, $(C_1-C_4)$alkylthio, $(C_1-C_4)$alkylamino or $(C_1-C_4)$dialkylamino and Z has the meanings given under formula (V), reacting the compound of the formula X with an amine of the formula VI, and, if appropriate, carbamoylating the resulting compound of the formula I' on the nitrogen or, if $R^3$ is hydrogen, chlorinating or brominating the compound.

As regards the reaction conditions, both reaction steps can be carried out using the same solvents, auxiliary bases and reaction temperatures as in the case of the above-described preparation of the compounds of the formula I from the compounds of the formulae V and VI.

Both reaction steps can be carried out without working-up after the first reaction step in the form of a one-pot reaction.

The starting compounds of the formula V can be prepared analogously to known processes. The starting materials used are acetoacetate derivatives which are converted into the chloropyrimidines via the corresponding hydroxypyrimidines:

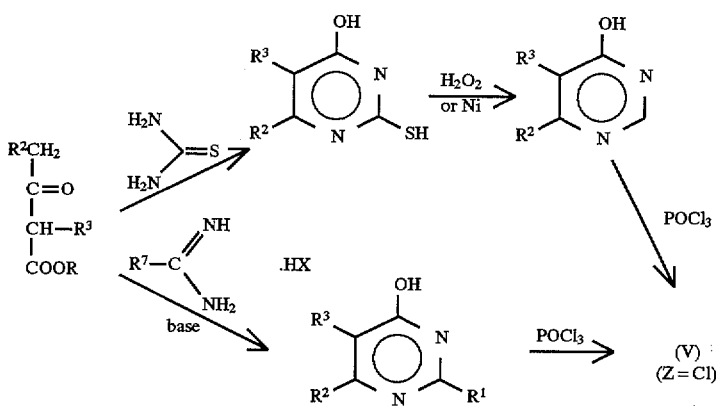

The starting compounds of formula VII can be obtained from malonate derivatives in analogy to known processes:

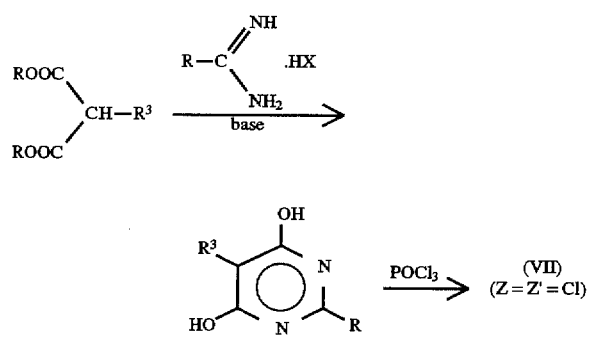

The amines of the formula VI which are required as starting materials can be prepared by known processes.

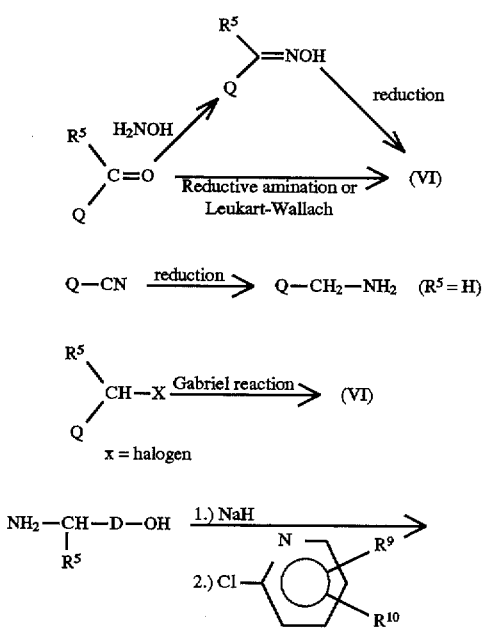

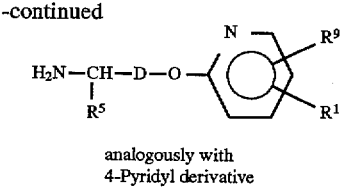

analogously with 4-Pyridyl derivative

If appropriate, the compounds of the formula I in which $R^3$ is hydrogen can be halogenated by known processes.

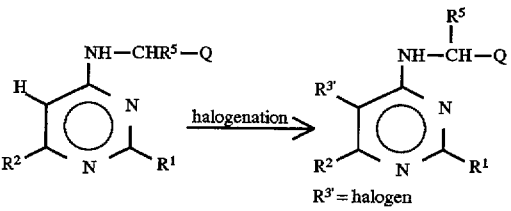

The active substances are well tolerated by plants and are suitable for controlling animal pests, in particular insects, arachnids, helminths and molluskcs, very particularly preferably for controlling insects and arachnids which occur in agriculture, in livestock breeding, in forests, in the protection of stored products and materials, and in the hygiene field.

Mention must be made of the property of the active substances to be taken up by the plant via stalks and leaves and to be transported down to the roots by means of basipetal transport, thus allowing an effective control of nematodes.

The active substances are active against normally sensitive and resistant species and all or some development stages. The abovementioned pests include:

From the order of the Acarina, for example, *Acarus siro, Agras spp., Ornithrodoros spp., Dermanyssus gallinae, Eriophyes ribis, Phyllocoptruta oleivora, Boophilus spp., Rhipicephalus spp., Amblyomma spp., Myalomma spp., Ixodes spp., Psoroptes spp., Chorioptes spp., Sarcoptes spp., Tarsonemus spp., Bryobia praetiosa, Panonychus spp., Tetranychus spp., Eotetranychus spp., Oligonychus spp., Eutetranychus spp.*

From the order of the Isopoda, for example, *Oniscus asselus, Armadium vulgare, Porcellio scaber.*

From the order of the Diplopoda, for example, *Blaniulus guttulatus,*

From the order of the Chilopoda, for example, *Geophilus carpophagus, Scutigera spp.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blatella germanica, Acheta domesticus, Gryllotalpa spp., Locusta migratoria migratorioides, Melanoplus differentialis, Schistocerca gregarai.*

From the order of the Dermaptera, for example, *Forficula auricularia.*

From the order of the Isoptera, for example, *Reticulitermes spp.*

From the order of the Anoplura, for example, *Phylloera vastatrix, Pemphigus spp., Pediculus humanus corpotis, Haematopinus spp., Linognathus spp.*

From the order of the Mallophaga, for example, *Trichodectes spp., Damalinea spp.*

From the order of the Thysanoptera, for example, *Hercinothrips femoralis, Thrips tabaci.*

From the order of the Heteroptera, for example, *Eurygaster spp., Dysdercus intermedius, Piesma quadrata, Cimex lectularius, Rhodnius prolixus, Triatoma spp.*

From the order of the Homoptera, for example, *Aleurodes brassicae, Bemisia tabaci, Trialeurodes vaporarium, Aphis gossypii, Bravicornyne brassicae, Cryptomyzus ribis, Doralis fabae, Doralis pomi, Eriosoma lanigerum, Hyalopterus arundinis, Macrosiphium avenae, Myzus spp., Phorodon humuli, Rhopalosiphum padi, Empoasca spp., Euscelus bilobatus, Naphotettix cincticeps, Lecanium corni, Saissetia oleae, Laodelphax striatellus, Nilaparvata lugens, Aonidiella auroantii, Apidiotus hederae, Pseudococcus spp., Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, Malacosma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cocoecia podana, Capua reticulana, Choristoneura fumiferana, Clysia ambiguella, Momona magnanima, Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylloides chrysocephala, Epilachna varivestis, Atomaria spp., Oryzaephilus surinamensis, Anthonumus spp., Sitophilus spp., Otiorrhynchus sulcatus, Cosmopolites sordidus, Ceuthorrhynchus assimilis, Hypera postica, Dermestes spp., Trogoderma, Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis, Costelytra zealandica.*

From the order of the Hymenoptera, for example, Diprion spp., Hoplocampa spp., Lasius spp., Monomorium pharaonis, Vespa spp.

From the order of the Diptera, for example, Aedes spp., Anopheles spp., Culex spp., Drosophila melanogaster, Musca spp., Fannia spp., Calliophora erythrocephala, Lucilia spp., Chrysomyia spp., Cuterebra spp., Gastrophilus spp., Hypobosca spp., Stomoxys spp., Oestrus spp. Hypoderma spp., Tabanus spp., Tannia spp., Bibio hortulanus, Oscinella frit, Phorbia spp., Pegomyia hyoscyami, Ceratitis capitata, Dacus oleae, Tripula paludosa.

From the order of the Siphonaptera, for example, Xenopsylla cheopsis, Ceratophyllus spp.

From the order of the Arachnida, for example, *Scorpio maurus, Latrodectus mactans.*

From the class of the helminths, for example, Haemonchus, Trichostrongulus, Ostertagia, Cooperia, Chabertia, Strongyloides, Oesophagostomum, Hyostrongulus, Ancylostoma, Ascaris and Heterakis as well as Fasciola and nematodes which are harmful to plants, for example those from the genera Meloidogyne, Heterodera, Ditylenchus, Aphelenchoides, Radopholus, Globodera, Pratylenchus, Longidorus and Xiphinema.

From the class of the gastropods, for example Deroceras spp., Arion spp., Lymnaea spp., Galba spp., Succinea spp., Biophalaria spp., Bulinus spp., Oncomelania spp.

From the class of the bivalves, for example Dreissena spp.

The invention also relates to insecticidal and acaricidal agents which contain the compounds of the formula I besides suitable formulation auxiliaries.

The agents according to the invention generally contain the active substances of the formula I in amounts of 1 to 95% by weight.

They can be formulated in various ways, depending on the prevailing biological and/or chemicophysical parameters. Examples of possible formulations which are suitable are: wettable powders (WP), emulsifiable concentrates (EC), aqueous solutions (SC), emulsions, sprayable solutions, dispersions on an oil or water basis (SC), suspoemulsions (SC), dusts (DP), seed-dressing agents, granules in the form of microgranules, spray granules, coated granules and adsorption granules, water-dispersible granules (WG), ULV formulations, microcapsules, waxes or baits.

These individual formulation types are known in principle and are described, for example, in:

Winnacker-Küchler, "Chemische Technologie" [Chemical Technology], Volume 7, C. Hauser Verlag, Munich, 4th Edition 1986; van Falkenberg, "Pesticides Formulations" Marcel Dekker, N.Y., 2nd Ed. 1972–73; K. Martens, "Spray Drying Handbook", 3rd Ed. 1979, G. Goodwin Ltd. London.

The necessary formulation auxiliaries such as inert materials, surfactants, solvents and other additives are also known and are described, for example, in: Watkins, "Handbook of Insecticide Dust Diluents and Carriers", 2nd Ed., Darland Books, Caldwell N.J.; H.v. Olphen, "Introduction to Clay Colloid Chemistry"; 2nd Ed., J. Wiley & Sons, N.Y.; Marsden, "Solvents Guide", 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Based on these formulations, it is also possible to prepare combinations with other pesticidally active substances, fertilizers and/or growth regulators, for example in the form of a readymix or a tank mix. Wettable powders are preparations which are uniformly dispersible in water and which, besides the active substance, also contain wetting agents, for example, polyoxyethylated alkylphenols, polyoxyethylated fatty alcohols, alkylsulfonates or alkylphenolsulfonates, and dispersing agents, for example sodium ligninsulfonate, sodium 2,2'-dinaphthylmethane-6,6'-disulfonate, sodium dibutylnaphthalenesulfonate and also sodium oleylmethyltaurinate, in addition to a diluent or inert substance. Emulsifiable concentrates can be prepared, for example, by dissolving the active substance in an organic solvent, for example butanol, cyclohexanone, dimethylformamide, xylene and also higher-boiling aromatics or hydrocarbons, with the addition of one or more emulsifiers. Emulsifiers which can be used are, for example: calcium salts of alkylarylsulfonic acids, such as calcium dodecylbenzenesulfonate or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc or natural clays, such as kaolin, bentonite or pyrophillite, or diatomaceous earth. Granules can be produced either by spraying the active substance onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

The active substance concentration in wettable powders is, for example, about 10 to 90% by weight; the remainder to 100% by weight is composed of conventional formulation components. In the case of emulsifiable concentrates, the active substance concentration can be about 5 to 80% by weight. Formulations in the form of dusts usually contain 5 to 20% by weight of active substance, sprayable solutions about 2 to 20% by weight. In the case of granules, the active substance content depends partly on whether the active compound is liquid or solid and on which granulation auxiliaries, fillers etc. are used.

In addition, the active substance formulations mentioned comprise, if appropriate, the adhesives, wetting agents, dispersing agents, emulsifiers, penetrants, solvents, fillers or carriers which are conventional in each case.

For use, the concentrates which are present in commercially available form are diluted, if appropriate, in a conventional manner, for example using water in the case of wettable powders, emulsifiable concentrates, dispersions and, in some cases, also in the cast of microgranules. Preparations in the form of dusts and granules and also sprayable solutions are usually not further diluted with other inert substances before use.

The application rate required varies with the external conditions, such as, inter alia, temperature and humidity. It can vary within wide limits, for example between 0.005 and 10.0 kg/ha or more of active ingredient; preferably, however, it is between 0.01 and 5 kg/ha.

The active substances according to the invention can exist, in their commercially available formulations and in the use forms prepared from these formulations, as mixtures with other active substances such as insecticides, attractants, sterilants, acaricides, nematicides, fungicides, growth-regulating substances or herbicides.

The pesticides include, for example, phosphates, carbamates, carboxylates, formamidines, tin compounds, substances produced by microorganisms, and others. Preferred components in the mixtures are 1. from the group of the phosphorus compounds acephate, azamethiphos, azinphos-ethyl, azinphos-methyl, bromophos, bromophos-ethyl, clorfenvinphos, chlormephos, chlorpyrifos, chlorpyrifos-methyl, demeton, demeton-S-methyl, demeton-s-methyl sulfone, dialifos, diazinone, dichlorvos, dicrotophos, O,O-1,2,2,2-tetrachloroethylphosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidation, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos-ethyl, pirimiphosmethyl, profenofos, propaphos, proetamphos, prothiofos, pyraclofos, pyridapenthion, quinalphos, sulprofos, temephos, terbufos, tetrachlorvinphos, thiometon, triazophos, trichlorophon, vamidothion;

2. from the group of the carbamates aldicarb, 2-sec.-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cu-menylbutyryl (methyl)carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio)ethylideneamino)-N-methyl-N-(morpholinothio)carbamate (UC 51717);

3. from the group of the carboxylates allethrin, alphamethrin, 5-benzyl-3-furylmethyl (E)-(1R)-cis-2,2-dimethyl-3-(2-oxothiolan-3-ylidenemethyl) cyclopropanecarboxylate, bioallethrin, bioallethrin ((S)-cyclopentylisomer), bioresmethrin, biphenate, (RS)-1-cyano-1-(6-phenoxy-2-pyridyl) methyl (1RS)-trans-3-(4-tert.-butylphenyl)-2,2-dimethylcyclopropanecarboxylate (NCI 85193), cycloprothrin, cyfluthrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R) isomer), d-pralethrin, pyrethrins (natural products), resmethrin, tefluthrin, tetramethrin, tralomethrin;

4. from the group of the amidines amitraz, chlordimeform;

5. from the group of the tin compounds cyhexatin, fenbutatin oxide;

6. others abamectin, bacillus thuringiensis, bensultap, binapacryl, bromopropylate, buprofezin, camphechlor, cartap, chlorobenzilate, chlorfluazuron, 2-(4-chlorophenyl)-4,5-diphenylthiophene (UBI-T 930), chlorfentezine, 2-naphthylmethyl cyclopropane carboxylate (Ro 12-0470), cyromazin, ethyl N-(3,5-dichloro-4-(1,1,2,3,3,3-hexafluoro-1-propyloxy)phenyl)carbamoyl)-2-chlorobenzocarboximidate, DDT, dicofol, N-(N-3,5-dichloro-4-(1,1,2,2-tetrafluoroethoxy)phenylamino)carbonyl-2,6-difluorobenzamide (XRD 473), diflubenzuron, N-(2,3-Dihydro-3-methyl-1,3-thiazol-2-ylidene)-2,4-xylidine, dinobuton, dinocap, endosulfan, ethofenprox, (4-ethoxyphenyl)(dimethyl)(3-(3-phenoxyphenyl)propyl) silane, (4-ethoxyphenyl)(3-(4-fluoro-3-phenoxyphenyl) propyl)dimethylsilane, fenoxycarb, 2-fluoro-5-(4-(4-ethoxyphenyl)-4-methyl-1-pentyl)diphenyl ether (MTI 800), granulosis and nuclear polyhedrosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro-6H-thiazine (SD 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, triflumuron.

The active substance content of the use forms prepared from the commercially available formulations can be from 0.00000001 to 100 percent of active substance, preferably between 0.00001 and 1% by weight.

Application is effected in a customary manner adapted to suit the use forms.

The active substances according to the invention are also suitable for controlling endoparasites and ectoparasites in the field of veterinary medicine or in the field of animal keeping.

Here, the active substances according to the invention are administered in a known manner, such as oral administration in the form of, for example, tablets, capsules, drinks, granules, by dermal administration, for example in the form of dipping, spraying, pouring-on and spotting-on and powdering, and by parenteral administration, for example in the form of an injection.

Accordingly, the novel compounds of the formula I according to the invention can also be employed particularly advantageously in livestock keeping (for example cattle, sheep, pigs and poultry such as chickens, geese etc). In a preferred embodiment of the invention, the novel compounds, if appropriate in suitable formulations (cf. above) and if appropriate together with the drinking water or feed, are administered orally to the animals. Since they are excreted effectively with the feces, the development of insects in the feces of animals can be prevented very simply in this fashion. The dosage rates and formulations which are suitable in each case depend, in particular, on the species and the development stage of the livestock and also on the infection pressure, and they can be determined and chosen easily by the customary methods. For example, the novel compounds can be used in cattle in dosage rates of from 0.01 to 1 mg/kg of body weight.

The compounds of the formula I according to the invention are distinguished by an outstanding fungicidal action. Fungal pathogens which have already penetrated the plant tissue can be controlled successfully in a curative manner. This is particularly important and advantageous in the case of those fungal diseases where control with fungicides which are otherwise customary is no longer effective once infection has taken place. The spectrum of action of the claimed compounds embraces a large number of a wide range of economically important phytopathogenic fungi such as, for example, *Pyricularia oryzae, Venturia inaequalis, Cercospora beticola*, powdery mildew species, Fusarium species, *Plasmopara viticola*, various rusts and *Pseudocercosporella herpotrichoides*.

Besides, the compounds according to the invention are also suitable for use in industrial fields, for example as wood preservatives, as preservatives in paints, in cooling lubricants for metalworking, or as preservatives in drilling and cutting oils.

The invention also relates to fungicidal agents which contain the compounds of the formula I besides suitable formulation auxiliaries. The agents according to the invention generally contain the active substances of the formula I in amounts of 1 to 95% by weight.

They can be formulated in a variety of ways, as predetermined by the biological and/or chemicophysical parameters. The following possibilities are therefore suitable for formulation: wettable powders (WP), emulsifiable concentrates (EC), aqueous dispersions on an oil or water base (SC), suspoemulsions (SC), dusts (DP), seed-dressing agents, granules in the form of water-dispersible granules (WG), ULV formulations, microcapsules, waxes or baits.

These individual formulation types are known in principle and are described, for example, in: Winnacker-Küchler, "Chemische Technologie", [Chemical Technology], Volume 7, C. Hauser Verlag, Munich, 4th Ed. 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The necessary formulation auxiliaries such as inert materials, surfactants, solvents and other additives are also known and are described, for example, in: Watkins, "Handbook of Insecticide Dust Diluents and Carriers", 2nd Ed., Darland Books, Caldwell N.J.; H.v.01phen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts]", Wiss. Verlagsgesell., Stuttgart 1976; Winnacker-Küchler, "Chemische Technologie [Chemical Technology]", Volume 7, C. Hauser Verlag, Munich, 4th Ed. 1986.

Based on these formulations, it is also possible to prepare combinations with other pesticidally active substances, fertilizers and/or growth regulators, for example in the form of a readymix or a tank mix. Wettable powders are preparations which are uniformly dispersible in water and which, besides the active substance, also contain wetting agents, for example, polyoxyethylated alkylphenols, polyoxyethylated fatty alcohols, alkylsulfonates or alkylphenolsulfonates, and dispersing agents, for example sodium ligninsulfonate, sodium 2,2'-dinaphthylmethane-6,6'-disulfonate, sodium dibutylnaphthalenesulfonate and also sodium oleylmethyltaurinate, in addition to a diluent or inert substance. Emulsifiable concentrates can be prepared, for example, by dissolving the active substance in an organic solvent, for example butanol, cyclohexanone, dimethylformamide, xylene and also higher-boiling aromatics or hydrocarbons, with the addition of one or more emulsifiers. Emulsifiers which can be used are, for example: calcium salts of alkylarylsulfonic acids, such as calcium dodecylbenzenesulfonate or non-ionic emulsifiers, such as fatty acid polyglycol esters, alkylaryl polyglycol ethers, fatty alcohol polyglycol ethers, propylene oxide/ethylene oxide sorbitan fatty acid esters, polyoxyethylene sorbitan fatty acid esters or polyoxyethylene sorbitol esters.

Dusts are obtained by grinding the active substance with finely divided solid substances, for example talc or natural clays, such as kaolin, bentonite or pyrophillite, or diatomaceous earth. Granules can be produced either by spraying the active substance onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

The active substance concentration in wettable powders is, for example, about 10 to 90% by weight; the remainder to 100% by weight is composed of conventional formulation components. In the case of emulsifiable concentrates, the active substance concentration can be about 5 to 80% by weight. Formulations in the form of dusts usually contain 5 to 20% by weight. In the case of granules, the active substance content depends partly on whether the active compound is liquid or solid and on which granulation auxiliaries, fillers etc. are used.

In addition, the active substance formulations mentioned contain, if appropriate, the adhesives, wetting agents, dispersing agents, emulsifiers, penetrants, solvents, fillers or carriers which are conventional in each case.

For use, the concentrates which are present in commercially available form are diluted, if appropriate, in a conventional manner, for example using water in the case of wettable powders, emulsifiable concentrates, dispersions and, in some cases, also in the case of microgranules. Preparations in the form of dusts and granules and also sprayable solutions are usually not further diluted with other inert substances before use.

The application rate required varies with the external conditions, such as, inter alia, temperature and humidity. It can vary within wide limits, for example between 0.005 and 10.0 kg/ha or more of active ingredient; preferably, however, it is between 0.01 and 5 kg/ha.

The active substances according to the invention can be used in their commercially available formulations either on their own or in combination with other fungicides known from the literature.

Suitable fungicides which are known from the literature and which can be combined according to the invention with the compounds of the formula I are anilazine, benalaxyl, benodanil, benomyl, binapacryl, bitertanol, buthiobat, captafol, captan, carbendazim, carboxin, CGD-94240 F, chlobenzothiazone, chlorthalonil, cymoxanil, cyproconazole, cyprofuram, dichlofluanid, dichlomezin, diclobutrazol, diethofencarb, difluconazole, dimethirimol, dimethomorph, diniconazole, dinocap, dithianon, dodemorph, dodine, edifenfos, ethirimol, etridiazol, fenarimol, fenfuram, fenpiclonil, fenpropidin, fenpropomorph, fentin acetate, fentin hydroxide, fluaziram, fluobenzimine, fluorimide, flusilazole, flutolanil, flutriafol, folpet, fosetylaiuminium, fuberidazole, furalaxyl, furmecyclox, guazatine, hexaconazole, imazalil, iprobenfos, iprodione, isoprothiolane, copper compounds such as copper oxychloride, oxine-copper, copper oxides, mancozeb, maneb, mepronil, metalaxyl, methasulfocarb, methfuroxam, myclobutanil, nabam, nitrothalidopropyl, nuarimol, ofurace, oxadixyl, oxycarboxin, penconazol, pencycuron, PP 969, probenazole, probineb, prochloraz, procymidon, propamocarb, propiconazol, prothiocarb, pyracarbolid, pyrifenox, pyroquilon, rabenzazole, schwefel, tebuconazole, thiabendazole, thiophanate-methyl, thiram, tolclofos-methyl, tolylfluauld, triadimefon, triadimenol, tricyclazole, tridemorph, triflumizol, triforine, vinchlozolin, zineb, Sodium dodecyl sulfonate, sodium dodecyl sulfate, sodium C13/C15-alcohol ether sulfonate, sodium cetostearyl phosphate dioctyl sodium sulfosuccinate, sodium isopropylnaphthalene sulfonate, sodium methylenebisnaphthalene sulfonate, cetyltrimethylammoniumchloride salts of long-chain primary, secondary or tertiary amines, alkylpropyleneamines, laurylpyrimidiniumbromide, ethoxylated quaternized fatty amines, alkyldimethylbenzylammonium chloride and 1-hydroxyethyl-2-alkylimidazoline.

The abovementioned components are known active substances, most of which are described in C. R. Worthing, S. B. Walker, The Pesticide Manual, 7th Edition (1983), British Crop Protection Council.

Moreover, the active substances according to the invention, in particular those of the examples mentioned, can exist, in their commercially available formulations and in the use forms prepared from these formulations, as a mixture with other active substances such as insecticides, attractants, sterilants, acaricides, nematicides, fungicides, growth-regulating substances or herbicides.

The active substance content of the use forms prepared from the commercially available formulations can vary within wide limits; the active substance concentration of the use forms can be between 0.0001 to 100% by weight, preferably between 0.001 and 1% by weight. Application is effected in a customary manner adapted to suit the use forms. The examples which follow are intended to illustrate the invention.

A) Formulation examples a) A dust is obtained by mixing 10 parts by weight of active substance and 90 parts by weight of talc as inert substance and comminuting the mixture in a hammer mill.

b) A wettable powder which is readily dispersible in water is obtained by mixing 25 parts by weight of active substance, 65 parts by weight of kaolin-containing quartz as inert substance, 10 parts by weight of potassium ligninsulfonate and 1 part by weight of sodium oleoylmethyltaurinate as wetting and dispersing agent, and grinding the mixture in a pinned disk mill.

c) A dispersion concentrate which is readily dispersible in water is obtained by mixing 40 parts by weight of active substance with 7 parts by weight of a sulfosuccinic monoester, 2 parts by weight of a sodium ligninsulfonate and 51 parts by weight of water and grinding the mixture in a ball mill to a fineness of below 5 microns.

d) An emulsifiable concentrate can be prepared from 15 parts by weight of active substance, 75 parts by weight of cyclohexanone as solvent and 10 parts by weight of ethoxylated nonylphenol (10 EO) as emulsifier.

e) Granules can be prepared from 2 to 15 parts by weight of active substance and an inert granule carrier material such as attapulgite, pumice granules and/or quartz sand. It is expedient to use a suspension of the wettable powder from Example b) with a solids content of 30 percent which is sprayed onto the surface of attapulgite granules, dried and intimately mixed. The percentage by weight of the wettable powder is approx. 5% and that of the inert carrier material approx. 95% of the finished granules.

B) Chemical examples

Example A

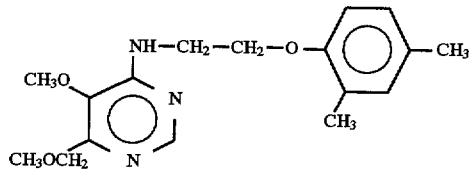

A mixture of 3.8 g (0.02 mol) of 4-chloro-5-methoxy-6-methoxymethylpyrimidine and 6.6 g (0.04 mol) of 2-(2,4-dimethylphenoxy)ethylamine was heated for 2 hours at 100°. After cooling, the mixture was taken up in a water/methylene chloride mixture, the organic phase was washed several times with water, dried and concentrated. For purification, the crude product was chromatographed on silica gel using ethyl acetate.

Yield: 4.1 g (64.6% of theory) of 5-methoxy-6-methoxymethyl-4-[2-(2,4-dimethylphenoxy)-ethylamino]-pyrimidine of melting point 49°–50° C.

Preparation of the starting compound 4-chloro-5-methoxy-6-methoxymethylpyrimidine 85.0 g (0.5 mol) of 4-hydroxy-5-methoxy-6-methoxymethylpyrimidine were suspended in 600 ml of dichloroethane, 50.5 g of triethylamine were added, and 260 g (1.7 mol) of phosphorus oxychloride were then added without cooling. The mixture was stirred for 3 hours at 80° C., poured into ice-water and neutralized by adding solid sodium carbonate, the organic phase was separated, and the water phase was extracted several times by stirring with methylene chloride. The combined organic phases were dried and concentrated. The residue was distilled under a water pump vacuum. 66.1 g (70% of theory) of a yellow oil were obtained. B.p. 93°–96° C./0.1mm.

Preparation of 4-hydroxy-5-methoxy-6-methoxymethylpyrimidine

To 750 ml of 12% strength hydrogen peroxide, heated to 80° C., there were added in portions 101 g (0.5 mol) of 4-hydroxy-2-mercapto-5-methoxy-6-methoxymethylpyrimidine in such a way that a temperature of 80° C. was maintained. Stirring was then continued for 2 hours at 80° C. After cooling, solid sodium disulfite was added until potassium iodide/starch paper no longer showed a reaction with peroxide, and the mixture was then neutralized by adding potassium carbonate. The water was distilled off, and the solid residue, to which a little ethanol had been added, was then suspended in methylene chloride and subjected to filtration with suction. After concentration of the filtrate, 63 g (70% of theory) of product of melting point 141°–143° C. were obtained.

Preparation of 4-Hydroxy-2-mercapto-5-methoxy-6-methoxymethylpyrimidine 352.0 g (2.0 mol) of dimethyl 2,4-dimethoxyacetate and 152.2 g of thiourea were introduced into 1.5 l of ethanol, 360.0 g (2.0 mol) of 30% strength sodium methylate solution were added, and the mixture was refluxed for 6 hours. The solvent was distilled off, and the residue was then taken up in water and brought to pH 5 using concentrated hydrochloric acid. The product which had precipitated was filtered off with suction. 300.0 g (74.2% of theory) of yellow crystals of melting point 187°–189° C. were obtained.

Example B

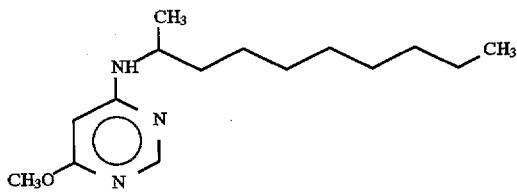

7.2 g ( 0.05 mol ) of 4-chloro-6-methoxypyrimidine and 15.7 g (0.1 mol) of 2-decylamine were heated at 100° C. for 2 hours. The mixture was worked up using a water/methylene chloride mixture, and purification by chromatography (silica gel/ethyl acetate) gave 8.0 g (58.8% of theory) of 4-(2-decylamino)-6-methoxypyrimidine in the form of a yellow oil.

Preparation of 4-chloro-6-methoxypyrimidine 22.4 g (0.15 mol) of 4,6-dichloropyrimidine were introduced into 250 ml of methanol. 27 g of a 30% strength sodium methylate solution were added dropwise at 0° C. After concentration, the mixture was worked up using a water/methylene chloride mixture. 15.0 g (69.2% of theory) of yellow crystals were obtained; m.p. 32°–34° C.

Example C

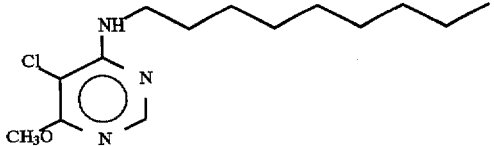

4.0 g (0.015 mol) of 4-(2-decylamino)-6-methoxypyrimidine were refluxed for 1 hour together with 2.2 g (0.016 mol) of N-chlorosuccinimide in 25 ml of chloroform. After cooling, the mixture was extracted by stirring with 2N sodium hydroxide solution, and the organic phase was dried and concentrated. 3.8 g (84.3% of theory) of 5-chloro-4-(2-decylamino)-6-methoxypyrimidine were obtained in the form of a yellow oil.

Example D

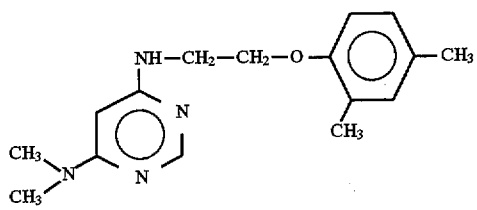

A solution of 8.3 g (0.05 mol) of 2-(2,4-dimethylphenoxy) ethylamine and 5.1 g (0.05 mol) of triethylamine in 50 ml of ethanol was added dropwise to a solution of 7.45 g (0.05 mol) of 4,6-dichloropyrimidine in 100 ml of ethanol at 20° C. The mixture was refluxed for 6 hours and, after cooling to room temperature, the dimethylamine was concentrated to saturation. It was again allowed to stand overnight, the solvent was then distilled off, the residue was taken up in a water/methylene chloride mixture, and the organic phase was dried and concentrated. After chromatographic purification of the crude product (silica gel/ethyl acetate), 6.0 g (41.9% of theory) of 6-dimethylamino-4-[2-(2,4-dimethylphenoxy)ethylamino]pyrimidine of melting point 115°–117° C. were obtained.

Example E

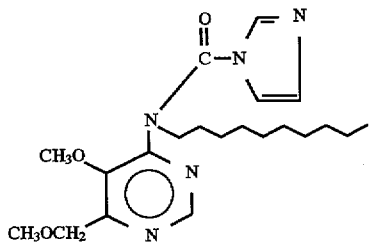

9.3 g (0.03 mol) of 4-(decylamino)-5-methoxy-6-methoxymethyl (prepared analogously to Example A from 1-decylamine and 4-chloro-5-methoxy-6-methoxymethylpyrimidine) 5 and 3.6 g (0.036 mol) of triethylamine in 20 ml of toluene were added dropwise at 5° C. to a solution of 4.0 g (0.02 mol) of diphosgene in 60 ml of toluene. The mixture was stirred for 6 hours at room temperature. 50 ml of water were added, and stirring was then continued for 2 hours at room temperature. The organic phase was dried and concentrated. 11.8 g of a brown oil (carbamoyl chloride) were obtained. This oil was dissolved in toluene, and the solution was added dropwise at room temperature to a solution of 3.5 g of imidazole and 5 g of triethylamine in 50 ml of toluene. Stirring was continued for 2 hours at room temperature, triethylamine hydrochloride was removed by filtration, and the filtrate was concentrated. After chromatographic purification (silica gel/ethyl acetate), 10.4 g (85.9% of theory) of N-decyl-N-(imidazol-1-ylcarbonyl)-5-methoxy-6-methoxymethylpyrimidine-4-amine were obtained in the form of a yellow oil.

Example F

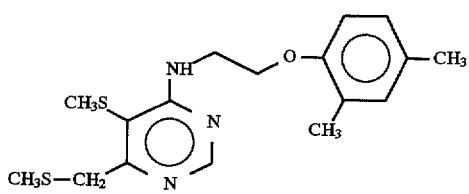

4.4 g (0.02 mol) of 4-chloro-5-methylthio-6-methylthiomethylpyrimidine and 7.4 g (0.045 mol) of 2-(2,4-dimethylphenoxy)ethylamine were heated for 2 hours at 100° C. The mixture was worked up using a water/methylene chloride mixture, and the organic phase was dried and concentrated. The crude product was purified by chromatography on silica gel (mobile phase, ethyl acetate/methanol (19:1)). 3.3 g (47.2% of theory) of 4-[2-(2,4-dimethylphenoxy)ethyl amino)-5-methylthio-6-methylthiomethylpyrimidine were obtained in the form of a yellow oil.

Preparation of the starting compound 4-chloro-5-methylthio-6-methylthiomethylpyrimidine The preparation was analogous to the synthesis of the starting compound 4-chloro-5-methoxy-6-methoxymethylpyrimidine, using 42 g of 4-hydroxy-5-methylthio-6-methylthiomethylpyrimidine Yield: 29.5 g (63.6% of theory) of crude product (was employed without further purification).

Preparation of 4-hydroxy-5-methylthio-6-methylthiomethylpyrimidine 180 g of 30% strength sodium methanolate solution were added dropwise at −10° C. to a solution of 52 g (0.5 mol) of formamidine acetate and 104 g (0.5 mol) of methyl 2,4-bis(mercaptomethyl)acetoacetate in 400 ml of methanol. Stirring was continued for 10 hours at room temperature, solids were filtered off, and the filtrate was concentrated. The resinous residue was taken up in approx. 150 ml of a 4:1 mixture of ethyl acetate and methanol. 42 g of colorless product (41.6 g of theory) crystallized out upon standing.

Example G

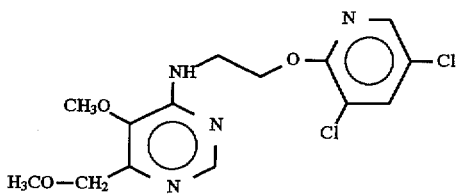

3.8 g (0.02 mol) of 4-chloro-5-methoxy-6-methoxymethylpyrimidine and 9.3 g (0.045 mol) of 2-(3,5-dichloropyridyl-2-oxy)ethylamine were reacted analogously to Example A. After chromatographic purification (silica gel/ethyl acetate) 4.5 g (62.6% of theory) of 4-[2-(3,5-dichloropyridyl-2-oxy)ethylamino]-5-methoxy-6-methoxymethylpyrimidine remained in the form of a brown oil which solidified gradually. M.p. 65°–66° C.

Preparation of 2-(3,5-dichloropyridyl-2-oxy)ethylamine 20.0 g (0.5 mol) of 60% sodium hydride (dispersion in mineral oil) were heated in 500 ml of dry dimethylacetamide to 50° C. 30.6 g (0.5 mol) of 2-aminoethanol were added dropwise to this mixture, which was stirred at 50° C. until the evolution of gas had ceased. After the mixture had cooled to room temperature, 91.2 g (0.5 mol) of 2,3,5-trichloropyridine were added in portions with occasional cooling. Stirring was then continued for 4 hours at 80° C. After working-up with a water/methylene chloride mixture and chromatographic purification of the crude product (silica gel/ethyl acetate/methanol 3:1), 40.0 g (38.6%) of a yellow oil were obtained.

Other examples can be found in Table A below. The radicals $R^1$ to $R^5$ and Q listed in the table correspond to the symbols in formula I

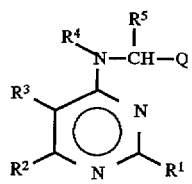 (I)

Table B contains compounds of the formula

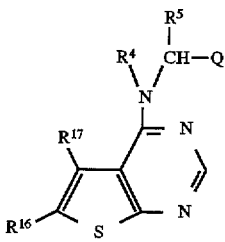

and Table C contains compounds of the formula

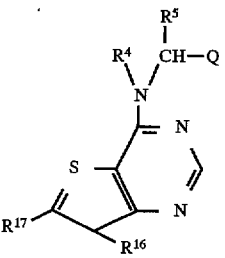

both of which are derived from formula I.

TABLE A

| Example No. | R¹ | R² | R³ | R⁴ | R⁵ | Q | M.P.[°C] |
|---|---|---|---|---|---|---|---|
| 1 | H | $CH_2OCH_3$ | $OCH_3$ | H | H | $-CH_2-O-\phantom{x}\text{C}_6\text{H}_5$ | Oil |
| 2 | H | $CH_2OCH_3$ | $OCH_3$ | H | H | $-CH_2-O-\text{(2-CH}_3\text{-C}_6\text{H}_4\text{)}$ | Oil |
| 3 | H | $CH_2OCH_3$ | $OCH_3$ | H | H | $-CH_2-O-\text{(4-CH}_3\text{-C}_6\text{H}_4\text{)}$ | Oil |
| 4 | H | $CH_2OCH_3$ | $OCH_3$ | H | H | $-CH_2-O-\text{(2-C}_2\text{H}_5\text{-C}_6\text{H}_4\text{)}$ | Oil |
| 5 | H | $CH_2OCH_3$ | $OCH_3$ | H | H | $-CH_2-O-\text{(3-C}_2\text{H}_5\text{-C}_6\text{H}_4\text{)}$ | 61–63 |
| 6 | H | $CH_2OCH_3$ | $OCH_3$ | H | H | $-CH_2-O-\text{(4-C}_2\text{H}_5\text{-C}_6\text{H}_4\text{)}$ | 64–66 |
| 7 | H | $CH_2OCH_3$ | $OCH_3$ | H | H | $-CH_2-O-\text{(2-CH}_3\text{CH}_2\text{CH}_2\text{-C}_6\text{H}_4\text{)}$ | Oil |

TABLE A-continued
| Example No. | R¹ | R² | R³ | R⁴ | R⁵ | Q | M.P.[°C.] |
|---|---|---|---|---|---|---|---|
| 8 | H | CH₂OCH₃ | OCH₃ | H | H |  | 65-66 |
| 9 | H | CH₂OCH₃ | OCH₃ | H | H |  | Oil |
| 10 | H | CH₂OCH₃ | OCH₃ | H | H |  | Oil |
| 11 | H | CH₂OCH₃ | OCH₃ | H | H |  | Oil |
| 12 | H | CH₂OCH₃ | OCH₃ | H | H |  | 77-79 |
| 13 | H | CH₂OCH₃ | OCH₃ | H | H |  | Oil |
| 14 | H | CH₂OCH₃ | OCH₃ | H | H |  | Oil |

TABLE A-continued
| Example No. | R¹ | R² | R³ | R⁴ | R⁵ | Q | M.P.[°C.] |
|---|---|---|---|---|---|---|---|
| 15 | H | CH₂OCH₃ | OCH₃ | H | H | 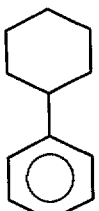 | Oil |
| 16 | H | CH₂OCH₃ | OCH₃ | H | H | 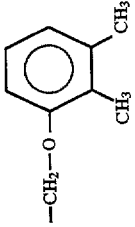 | Oil |
| 17 | H | CH₂OCH₃ | H | H | H | 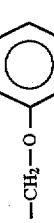 | 100–102 |
| 18 | H | CH₂OCH₃ | C₂H₅ | H | H | 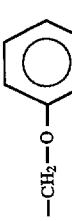 | 90–92 |
| 19 | SCH₃ | CH₂OCH₃ | OCH₃ | H | H | 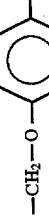 | Oil |
| 20 | H | CH₂OC₂H₅ | OC₂H₅ | H | H |  | Oil |
| 21 | H | CH₂OCH₃ | OCH₃ | H | H |  | 49–50 |

TABLE A-continued

| Example No. | R¹ | R² | R³ | R⁴ | R⁵ | Q | M.P.[°C.] |
|---|---|---|---|---|---|---|---|
| 22 | H | CH₂SCH₃ | SCH₃ | H | H | —CH₂—O—C₆H₃(CH₃)₂ (2,4-dimethyl) | Oil |
| 23 | CH₃ | CH₂OCH₃ | OCH₃ | H | H | —CH₂—O—C₆H₃(CH₃)₂ (2,4-dimethyl) | 87–89 |
| 24 | Cl | CH₂OCH₃ | OCH₃ | H | H | —CH₂—O—C₆H₃(CH₃)₂ (2,4-dimethyl) | |
| 25 | H | CH₂OCH₃ | OCH₃ | H | CH₃ | —CH₂—O—C₆H₃(CH₃)₂ (2,4-dimethyl) | Oil |
| 26 | H | CH₂OCH₃ | OCH₃ | H | H | —CH(CH₃)—O—C₆H₅ | 88–90 |
| 27 | H | CH₂OCH₃ | OCH₃ | H | H | —CH(CH₃)—O—C₆H₃(CH₃)₂ (2,4-dimethyl) | liquid |
| 28 | H | CH₂OCH₃ | OCH₃ | H | CH₃ | —CH(CH₃)—O—C₆H₃(CH₃)₂ (2,4-dimethyl) | Oil |

TABLE A-continued
| Example No. | R¹ | R² | R³ | R⁴ | R⁵ | Q | M.P.[°C.] |
|---|---|---|---|---|---|---|---|
| 29 | H | CH₂OCH₃ | OCH₃ | H | H | 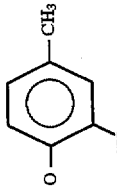 | Oil |
| 30 | H | CH₂OCH₃ | OCH₃ | H | H | 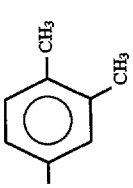 | 60-61 |
| 31 | H | CH₂OCH₃ | OCH₃ | H | H | 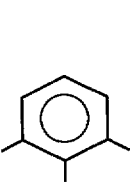 | Oil |
| 32 | H | CH₂OCH₃ | OCH₃ | H | H | 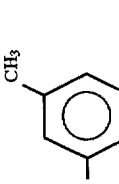 | Oil |
| 33 | H | CH₂OCH₃ | OCH₃ | H | H | 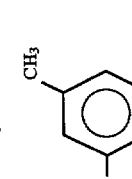 | 88-89 |

TABLE A-continued

| Example No. | R¹ | R² | R³ | R⁴ | R⁵ | Q | M.P.[°C.] |
|---|---|---|---|---|---|---|---|
| 34 | H | CH₂OCH₃ | OCH₃ | H | H | —CH₂—O—C₆H₃(CH₃)(CH(CH₃)₂) | Oil |
| 35 | H | CH₂OCH₃ | OCH₃ | H | H | —CH₂—O—C₆H₃(CH₃)(C(CH₃)₃) | Oil |
| 36 | H | CH₂OCH₃ | OCH₃ | H | H | —CH₂—O—C₆H₂(CH₃)₃ | 82-83 |
| 37 | H | CH₂OCH₃ | OCH₃ | H | H | —CH₂—O—C₆H₄(CF₃) | 79-80 |
| 38 | H | CH₂OCH₃ | OCH₃ | H | H | —CH₂—O—C₆H₄(CF₃) | 80-82 |
| 39 | H | CH₂OCH₃ | OCH₃ | H | H | —CH₂—O—C₆H₄(CF₃) | 96-97 |

TABLE A-continued

| Example No. | $R^1$ | $R^2$ | $R^3$ | $R^4$ | $R^5$ | Q | M.P.[°C.] |
|---|---|---|---|---|---|---|---|
| 40 | H | $CH_2OCH_3$ | $OCH_3$ | H | H | —$CH_2$—O—C₆H₃($CH_3$)($CF_3$) | Oil |
| 41 | H | $CH_2OCH_3$ | $OCH_3$ | H | H | —$CH_2$—O—C₆H₄(Cl) | Oil |
| 42 | H | $CH_2OCH_3$ | $OCH_3$ | H | H | —$CH_2$—O—C₆H₃(Cl)($CH_3$) | 76–78 |
| 43 | H | $CH_2OCH_3$ | $OCH_3$ | H | H | —$CH_2$—O—C₆H₃($CH_3$)(Cl) | Oil |
| 44 | H | $CH_2OCH_3$ | $OCH_3$ | H | H | —$CH_2$—O—C₆H₃($CH_3$)(Cl) | 79–81 |
| 45 | H | $CH_2OCH_3$ | $OCH_3$ | H | H | —$CH_2$—O—C₆H₃(F)($C_2H_5$) | Oil |
| 46 | H | $CH_2OCH_3$ | $OCH_3$ | H | H | —$CH_2$—O—C₆H₃(Cl)(Cl) | Oil |

TABLE A-continued
| Example No. | R¹ | R² | R³ | R⁴ | R⁵ | Q | M.P.[°C.] |
|---|---|---|---|---|---|---|---|
| 47 | H | CH₂OCH₃ | OCH₃ | H | H |  | 100–101 |
| 48 | H | CH₂OCH₃ | OCH₃ | H | H |  | Oil |
| 49 | H | CH₂OCH₃ | OCH₃ | H | H |  | |
| 50 | H | CH₂OCH₃ | OCH₃ | H | H |  | |
| 51 | H | CH₂OCH₃ | OCH₃ | H | H |  | |
| 52 | H | CH₂OCH₃ | OCH₃ | H | H |  | 53–55 |
| 53 | H | CH₂OCH₃ | OCH₃ | H | H |  | resin |

TABLE A-continued
| Example No. | $R^1$ | $R^2$ | $R^3$ | $R^4$ | $R^5$ | Q | M.P.[°C.] |
|---|---|---|---|---|---|---|---|
| 54 | H | $CH_2OCH_3$ | $OCH_3$ | H | H |  | resin |
| 55 | H | $CH_2OCH_3$ | $OCH_3$ | H | H | 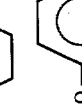 | resin |
| 56 | H | $CH_2OCH_3$ | $OCH_3$ | H | $C_2H_5$ |  | |
| 57 | H | $CH_2SCH_3$ | $SCH_3$ | H | $C_2H_5$ | 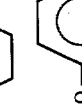 | |
| 58 | H | $CH_2OCH_3$ | $OCH_3$ | H |  |  | resin |
| 59 | H | $CH_2OCH_3$ | $OCH_3$ | H | H | $(CH_2)_8CH_3$ | Oil |
| 60 | H | $CH_2OCH_3$ | $OCH_3$ | H | H | $(CH_2)_8CH_3$ | Oil |
| 61 | H | $CH_2OCH_3$ | $OCH_3$ | 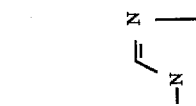 | $CH_3$ | $(CH_2)_8CH_3$ | Oil |
| 62 | H | $CH_2OCH_3$ | $OCH_3$ | H | $CH_3$ | $(CH_2)_7CH_3$ | Oil |
| 63 | H | $CH_2OCH_3$ | $OCH_3$ | 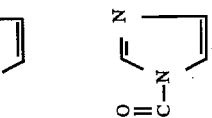 | $CH_3$ | $(CH_2)_7CH_3$ | Oil |
| 64 | H | $CH_2SCH_3$ | $SCH_3$ | H | $CH_3$ | $(CH_2)_7CH_3$ | Oil |

TABLE A-continued

| Example No. | R¹ | R² | R³ | R⁴ | R⁵ | Q | M.P.[°C.] |
|---|---|---|---|---|---|---|---|
| 65 | H | CH₃ | SCH₃ | H | CH₃ | (CH₂)₇CH₃ | Oil |
| 66 | H | OCH₃ | H | H | CH₃ | (CH₂)₇CH₃ | Oil |
| 67 | H | OCH₃ | Cl | H | CH₃ | (CH₂)₇CH₃ | Oil |
| 68 | H | OCH₃ | Br | H | CH₃ | (CH₂)₇CH₃ | Oil |
| 69 | H | OCH₃ | C₂H₅ | H | CH₃ | (CH₂)₇CH₃ | Oil |
| 70 | H | OCH₃ | OCH₃ | H | CH₃ | (CH₂)₇CH₃ | Oil |
| 71 | H | OC₂H₅ | H | H | CH₃ | (CH₂)₇CH₃ | Oil |
| 72 | H | OC₂H₅ | H | H | CH₃ | (CH₂)₈CH₃ | Oil |
| 73 | H | OCH₂CF₃ | H | H | CH₃ | (CH₂)₇CH₃ | Oil |
| 74 | H | OCH₂CF₃ | Cl | H | CH₃ | (CH₂)₇CH₃ | Oil |
| 75 | H | OCH₂CF₃ | H | H | CH₃ | (CH₂)₈CH₃ | Oil |
| 76 | H | N(CH₃)₂ | H | H | CH₃ | (CH₂)₇CH₃ | Oil |
| 77 | H | N(CH₃)₂ | Cl | H | CH₃ | (CH₂)₇CH₃ | Oil |
| 78 | H | N(CH₃)₂ | Br | H | CH₃ | (CH₂)₇CH₃ | Oil |
| 79 | H | N(CH₃)₂ | OCH₃ | H | CH₃ | (CH₂)₇CH₃ | Oil |
| 80 | H | N(CH₃)₂ | H | H | H | 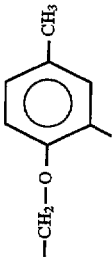 | 115–117 |
| 81 | H | N(CH₃)₂ | Cl | H | H | 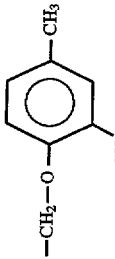 | 82–83 |
| 82 | H | N(CH₃)₂ | Br | H | H | 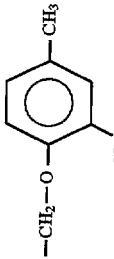 | resin |
| 83 | H | Cl | H | H | H | 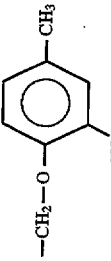 | 99–101 |

TABLE A-continued

| Example No. | R¹ | R² | R³ | R⁴ | R⁵ | Q | M.P.[°C.] |
|---|---|---|---|---|---|---|---|
| 84 | H | OCH₃ | OCH₃ | H | H | —CH₂—O—C₆H₃(CH₃)₂ (2,5-dimethylphenyl) | resin |
| 85 | H | CH₂OCH₃ | OCH₃ | H | H | —CH₂—O—C₆H₂(Cl)₂ (2,5-dichlorophenyl) | 69–70 |
| 86 | H | CH₂OCH₃ | OCH₃ | H | H | —CH₂—O—C₅H₃N(CF₃) (trifluoromethylpyridyl) | 111–113 |
| 87 | H | CH₂OCH₃ | OCH₃ | H | H | —CH₂—O—C₆H₄(CF₃) | Oil |
| 88 | H | CH₂OCH₃ | OCH₃ | H | H | —CH₂—O—C₆H₄—C₆H₅ (biphenyloxy) | |
| 89 | H | CH₂OCH₃ | OCH₃ | H | H | —CH₂—O-(2-naphthyl) | |
| 90 | H | CH₂OCH₃ | OCH₃ | H | H | —CH₂—O-(1-naphthyl) | |

TABLE A-continued

| Example No. | R¹ | R² | R³ | R⁴ | R⁵ | Q | M.P.[°C.] |
|---|---|---|---|---|---|---|---|
| 91 | H | CH₂OCH₃ | OCH₃ | H | H | —CH₂—O—(2,6-di-OCH₃-phenyl) | |
| 92 | H | OCH₃ | NO₂ | H | H | —CH₂—O—(2,5-di-CH₃-phenyl) | 101–103 |
| 93 | H | OCH₃ | NO₂ | H | CH₃ | (CH₂)₇CH₃ | Oil |
| 94 | H | CH₂OCH₃ | OCH₃ | H | H | (CH₂)₁₀CH₃ | Oil |
| 95 | H | CH₂OCH₃ | OCH₃ | H | H | (CH₂)₉CH₃ | Oil |
| 96 | H | CH₂OCH₃ | OCH₃ | H | H | (CH₂)₆CH₃ | Oil |
| 97 | H | CH₂OCH₃ | OCH₃ | H | H | (CH₂)₅CH₃ | Oil |
| 98 | H | CH₂OCH₃ | OCH₃ | H | H | (CH₂)₄CH₃ | Oil |
| 99 | H | CH₂OCH₃ | OCH₃ | H | H | (CH₂)₃CH₃ | |
| 100 | H | CH₂OCH₃ | OCH₃ | H | CH₃ | (CH₂)₉CH₃ | Oil |
| 101 | H | CH₂OCH₃ | OCH₃ | H | CH₃ | (CH₂)₆CH₃ | Oil |
| 102 | H | CH₂OCH₃ | OCH₃ | H | CH₃ | (CH₂)₅CH₃ | Oil |
| 103 | H | CH₂OCH₃ | OCH₃ | H | CH₃ | (CH₂)₄CH₃ | Oil |
| 104 | H | CH₂OCH₃ | OCH₃ | H | CH₃ | (CH₂)₃CH₃ | |
| 105 | H | CH₂OCH₃ | OCH₃ | H | CH₃ | (CH₂)₂CH₃ | |
| 106 | H | CH₂OCH₃ | OCH₃ | H | CH₃ | (CH₂)₂CH₃ | |
| 107 | H | CH₂OCH₃ | OCH₃ | H | CH₃ | (CH₂)₃—CH(CH₃)₂ | Oil |
| 108 | H | CH₂OCH₃ | OCH₃ | H | C₂H₅ | (CH₂)₃CH₃ | Oil |
| 109 | H | CH₂OCH₃ | OCH₃ | H | C₂H₅ | (CH₂)₆CH₃ | Oil |
| 110 | H | CH₂OCH₃ | OCH₃ | H | n-C₃H₇ | (CH₂)₅CH₃ | Oil |
| 111 | H | CH₂OCH₃ | OCH₃ | H | i-C₃H₇ | (CH₂)₇CH₃ | Oil |
| 112 | H | CH₂OHC₃ | OCH₃ | H | cyclopropyl | (CH₂)₇CH₃ | Oil |
| 113 | H | CH₂OCH₃ | OCH₃ | H | CH₃ | (CH₂)₂-phenyl | Oil |

TABLE A-continued

| Example No. | R¹ | R² | R³ | R⁴ | R⁵ | Q | M.P.[°C.] |
|---|---|---|---|---|---|---|---|
| 114 | H | CH₂OCH₃ | OCH₃ | H | CH₃ | –(CH₂)₂—OCH₂–phenyl | Oil |
| 115 | H | CH₂OCH₃ | OCH₃ | H | cyclohexyl | CH₃ R form | Oil |
| 116 | H | CH₂OCH₃ | OCH₃ | H | cyclohexyl | CH₃ S form | Oil |
| 117 | H | CH₂OCH₃ | OCH₃ | H | H | –CH(CH₃)–phenyl | Oil |
| 118 | H | CH₂OCH₃ | OCH₃ | H | H | –CH₂–phenyl | Oil |
| 119 | H | CH₂OCH₃ | OCH₃ | H | H | –CH₂–(4-t-Bu-phenyl) | 87–88 |
| 120 | H | CH₂OCH₃ | OCH₃ | H | CH₃ | –CH₂–(4-t-Bu-phenyl) | |
| 121 | H | CH₂OCH₃ | OCH₃ | H | H | –(CH₂)₂–(4-t-Bu-phenyl) | Oil |
| 122 | H | CH₂OCH₃ | OCH₃ | H | CH₃ | –(CH₂)₂–(4-t-Bu-phenyl) | Oil |
| 123 | H | OCH₃ | OCH₃ | H | H | (CH₂)₁₀CH₃ | |

TABLE A-continued

| Example No. | R¹ | R² | R³ | R⁴ | R⁵ | Q | M.P.[°C.] |
|---|---|---|---|---|---|---|---|
| 124 | H | OCH₃ | OCH₃ | H | H | (CH₂)₅CH₃ | |
| 125 | H | OCH₃ | OCH₃ | H | H | (CH₂)₇CH₃ | |
| 126 | H | OCH₃ | OCH₃ | H | H | (CH₂)₆CH₃ | |
| 127 | H | OCH₃ | OCH₃ | H | H | (CH₂)₆CH₃ | |
| 128 | H | OCH₃ | OCH₃ | H | H | (CH₂)₅CH₃ | |
| 129 | H | OCH₃ | OCH₃ | H | H | (CH₂)₄CH₃ | |
| 130 | H | OCH₃ | OCH₃ | H | H | (CH₂)₃CH₃ | |
| 131 | H | OCH₃ | OCH₃ | H | H | (CH₂)₉CH₃ | |
| 132 | H | OCH₃ | OCH₃ | H | CH₃ | (CH₂)₉CH₃ | |
| 133 | H | OCH₃ | OCH₃ | H | CH₃ | (CH₂)₆CH₃ | |
| 134 | H | OCH₃ | OCH₃ | H | CH₃ | (CH₂)₅CH₃ | |
| 135 | H | OCH₃ | OCH₃ | H | CH₃ | (CH₂)₄CH₃ | Oil |
| 136 | H | OCH₃ | OCH₃ | H | CH₃ | (CH₂)₃CH₃ | |
| 137 | H | OCH₃ | OCH₃ | H | CH₃ | (CH₂)₃CH₃ | |
| 138 | H | OCH₃ | OCH₃ | H | CH₃ | (CH₂)₂CH₃ | |
| 139 | H | OCH₃ | OCH₃ | H |  | (CH₂)₇CH₃ | Oil |
| 140 | H | CH₂OCH₃ | OCH₃ | H | H | 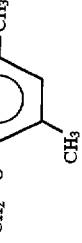 | |
| 141 | H | CH₂OCH₃ | OCH₃ | H | C₂H₅ | 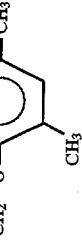 | |
| 142 | H | CH₂OCH₃ | OCH₃ | H | CH₃—CH—CH₃ | 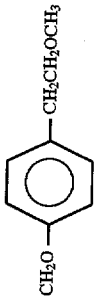 | Oil |
| 143 | CH₃ | CH₂OCH₃ | OCH₃ | H | CH₃ | (CH₂)₇CH₃ | Oil |
| 144 | H | CH₂OCH₃ | OCH₃ | H | H | 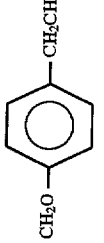 | Oil |

TABLE A-continued

| Example No. | R¹ | R² | R³ | R⁴ | R⁵ | Q | M.P.[°C.] |
|---|---|---|---|---|---|---|---|
| 145 | H | CH₂OCH₃ | OCH₃ | H | H | 4-(CH₂CH₂OC₂H₅)-phenyl-CH₂O— | Oil |
| 146 | H | CH₂OCH₃ | OCH₃ | H | H | 4-(CH₂CH₂OCH₃)-3-CH₃-phenyl-CH₂O— | Oil |
| 147 | H | CH₂OCH₃ | OCH₃ | H | H | 4-(CH₂CH₂OC₂H₅)-3-CH₃-phenyl-CH₂O— | Oil |
| 148 | H | CH₂OCH₃ | OCH₃ | H | H | 4-(CH₂CH₂OCH₃)-3,5-(CH₃)₂-phenyl-CH₂O— | Oil |
| 149 | H | CH₂OCH₃ | OCH₃ | H | H | 4-(CH₂CH₂OC₂H₅)-3,5-(CH₃)₂-phenyl-CH₂O— | Oil |
| 150 | H | CH₂OCH₃ | OCH₃ | H | C₂H₅ | 4-Cl-phenyl-O-(4-phenyl)— | |
| 151 | H | CH₂OCH₃ | OCH₃ | H | C₂H₅ | 4-CF₃-phenyl-O-(4-phenyl)— | |

TABLE A-continued
| Example No. | $R^1$ | $R^2$ | $R^3$ | $R^4$ | $R^5$ | Q | M.P.[°C.] |
|---|---|---|---|---|---|---|---|
| 152 | H | $CH_2OCH_3$ | $OCH_3$ | H | $C_2H_5$ | 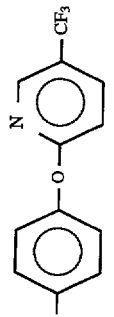 | |
| 153 | H | $CH_2OCH_3$ | $OCH_3$ | H | $C_2H_5$ | 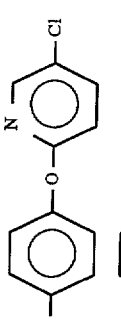 | |
| 154 | H | $CH_2OCH_3$ | $OCH_3$ | H | $C_2H_5$ | 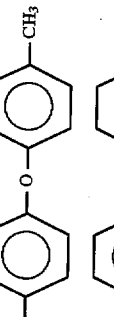 | Oil |
| 155 | H | $CH_2OCH_3$ | $OCH_3$ | H | $C_2H_5$ | 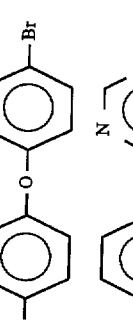 | |
| 156 | H | $CH_2OCH_3$ | $OCH_3$ | H | $C_2H_5$ | | |
| 157 | H | $CH_2OCH_3$ | $OCH_3$ | H | $C_2H_5$ |  | Oil |
| 158 | H | $CH_2OCH_3$ | $OCH_3$ | H | $C_2H_5$ |  | |

TABLE A-continued

| Example No. | R¹ | R² | R³ | R⁴ | R⁵ | Q | M.P.[°C.] |
|---|---|---|---|---|---|---|---|
| 159 | H | CH₂OCH₃ | H | H | C₂H₅ | 4-methylphenyl-O-(pyridin-2-yl with Cl, C₂H₅) | |
| 160 | H | CH₂OCH₃ | H | H | C₂H₅ | 4-methylphenyl-O-(pyridin-2-yl with CH₂OCH₃, OCH₃) | Oil |
| 161 | H | CH₂OCH₃ | H | H | C₂H₅ | 4-methylphenyl-O-CH₂-farnesyl | |
| 162 | H | CH₂OCH₃ | H | H | C₂H₅ | 4-methylphenyl-O-CH₂-geranyl | Oil |
| 163 | H | CH₂OCH₃ | H | H | C₂H₅ | 4-methylphenyl-O-(CH₂)₃CH₃ | |
| 164 | H | CH₂OCH₃ | H | H | C₂H₅ | 4-methylphenyl-O-CH₂CH₂-O-C₂H₅ | |
| 165 | H | SCH₃ | OCH₃ | H | CH₃ | (CH₂)₇CH₃ | Oil |
| 166 | H | C₂H₅ | C₂H₅ | H | CH₃ | (CH₂)₇CH₃ | Oil |
| 167 | H | H | OCH₃ | H | CH₃ | (CH₂)₇CH₃ | Oil |
| 168 | H | Cl | OCH₃ | H | CH₃ | (CH₂)₇CH₃ | Oil |
| 169 | H | OCH₃ | C₂H₅ | H | CH₃ | (CH₂)₇CH₃ | Oil |
| 170 | H | SCH₃ | C₂H₅ | H | CH₃ | (CH₂)₇CH₃ | Oil |
| 171 | H | Cl | H | H | CH₃ | (CH₂)₇CH₃ | Oil |
| 172 | H | CF₃ | Cl | H | CH₃ | (CH₂)₇CH₃ | Oil |
| 173 | H | CH₂OCH₃ | H | H | CH₃ | (CH₂)₇CH₃ | Oil |
| 174 | H | CH₂OCH₃ | Cl | H | CH₃ | (CH₂)₇CH₃ | Oil |
| 175 | H | CH₂OCH₃ | Cl | H | CH₃ | (CH₂)₇CH₃ | Oil |

TABLE A-continued

| Example No. | R¹ | R² | R³ | R⁴ | R⁵ | Q | M.P.[°C.] |
|---|---|---|---|---|---|---|---|
| 176 | H | H | OCH₃ | H | H | 2,4-dimethyl-5-(CH₂O-)phenyl | Oil |
| 177 | H | CH₂OCH₃ | OCH₃ | H | CH₃ | (CH₂)₃—C(CH₃)₂OH | |
| 178 | H | CH₂OCH₃ | OCH₃ | H | CH₃ | (CH₂)₂—O—CH₂CH(CH₃)₂ | Oil |
| 179 | H | CH₂OCH₃ | OCH₃ | H | C₂H₅ | (CH₂)₈CH₃ | Oil |
| 180 | H | CH₂OCH₃ | OCH₃ | H | n-C₃H₇ | (CH₂)₈CH₃ | Oil |
| 181 | H | CH₂OCH₃ | OCH₃ | H | n-C₈H₁₇ | (CH₂)₇CH₃ | Oil |
| 182 | H | CH₂OCH₃ | OCH₃ | H | n-C₅H₁₁ | (CH₂)₄CH₃ | Oil |
| 183 | H | CH₂OCH₃ | OCH₃ | H | C₂H₅ | 4-(quinoxalin-2-yloxy)phenyl | |
| 184 | H | CH₂OCH₃ | OCH₃ | H | C₂H₅ | 4-(pyrimidin-2-yloxy)phenyl | |
| 185 | H | CH₂OCH₃ | OCH₃ | H | C₂H₅ | 4-(pyrazin-2-yloxy)phenyl | Oil |
| 186 | H | CH₂OCH₃ | OCH₃ | H | C₂H₅ | 4-(3-methoxy-6-pyridazinyloxy)phenyl | |
| 187 | H | CH₂OCH₃ | OCH₃ | H | C₂H₅ | 4-(3-chloro-5-trifluoromethyl-2-pyridyloxy)phenyl | |

TABLE A-continued
| Example No. | $R^1$ | $R^2$ | $R^3$ | $R^4$ | $R^5$ | Q | M.P.[°C.] |
|---|---|---|---|---|---|---|---|
| 188 | H | $CH_2OCH_3$ | $OCH_3$ | H | $C_2H_5$ | 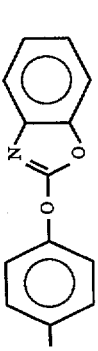 | |
| 189 | H | $CH_2OCH_3$ | $OCH_3$ | H | $C_2H_5$ | 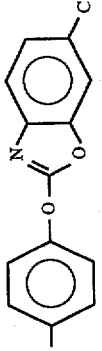 | |
| 190 | H | $CH_2OCH_3$ | $OCH_3$ | H | $C_2H_5$ | 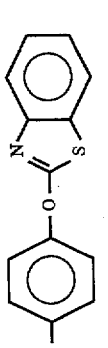 | |
| 191 | H | $CH_2OCH_3$ | $OCH_3$ | H | $C_2H_5$ | 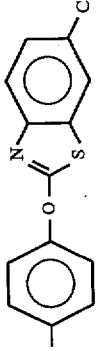 | |
| 192 | H | $CH_2OCH_3$ | $OCH_3$ | H | $C_2H_5$ | 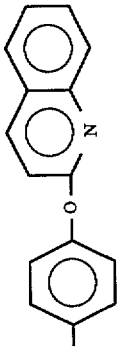 | |
| 192a | H | $CH_2OCH_3$ | $OCH_3$ | H | H | 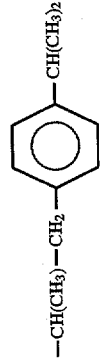 | Oil |
| 192b | H | $CH_2OCH_3$ | $OCH_3$ | H | H | 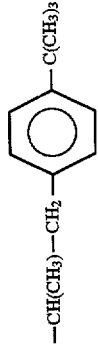 | Oil |
| 192c | H | $CH_2OCH_3$ | $OCH_3$ | H | $CH_3$ | 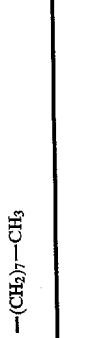 | |

TABLE B

| Example No. | R⁴ | R⁵ | R¹⁶ | R¹⁷ | Q | M.P.[°C.] |
|---|---|---|---|---|---|---|
| 193 | H | CH₃ | CH₃ | H | —(CH₂)₇CH₃ | 100–103 |
| 194 | H | CH₃ | CH₃ | H | —(CH₂)₈CH₃ | 95–97 |
| 195 | H | H | CH₃ | CH₃ | —(CH₂)₁₀CH₃ | 67–68 |
| 196 | H | H | CH₃ | CH₃ | —(CH₂)₄CH₃ | 83–85 |
| 197 | H | C₂H₅ | CH₃ | CH₃ | —C₆H₄—O—C₆H₄—F | |
| 198 | H | CH₃ | H | H | (CH₂)₇CH₃ | |
| 199 | H | CH₃ | H | H | (CH₂)₆CH₃ | |
| 200 | H | C₂H₅ | H | H | —C₆H₄—O—C₆H₄—F | |
| 201 | H | C₂H₅ | H | H | —C₆H₄—O—C₆H₄—Cl | |
| 202 | H | | H | H | —C₆H₄—O—C₆H₄—Cl | |

TABLE C

| Example No. | R⁴ | R⁵ | R¹⁶ | R¹⁷ | Q | M.P.[°C.] |
|---|---|---|---|---|---|---|
| 203 | H | CH₃ | H | H | —(CH₂)₈CH₃ | 69–72 |
| 204 | H | CH₃ | H | H | —(CH₂)₇CH₃ | 100–103 |
| 205 | H | CH₃ | H | H | —(CH₂)₆CH₃ | |
| 206 | H | C₂H₅ | H | H | —C₆H₄—O—C₆H₄—F | |
| 207 | H | C₂H₅ | H | H | —C₆H₄—O—C₆H₄—Cl | |
| 208 | H | cyclopropyl | H | H | (CH₂)₇CH₃ | |

C) Biological examples

Example 1

Wheat plants in the 3-leaf stage were heavily inoculated with conidia of powdery mildew of wheat (*Erysiphe graminis*) and placed in a greenhouse at 20° C. and a relative atmospheric humidity of 90–95%. 3 days after inoculation, the plants were uniformly wetted with the compounds shown in Tables A–C at the indicated active substance concentrations. After an incubation time of 10 days, the plants were investigated for attack with powdery mildew of wheat. The degree of attack is expressed in % of attacked leaf surface, relative to untreated, infected control plants (=100% attack). The result is summarized in Table 1.

TABLE 1

| Compounds according to Example No. | leaf surface infested with powdery mildew of wheat in % at mg of active substance/liter of spray liquor | | | |
|---|---|---|---|---|
| | 500 | 250 | 125 | 60 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| 6 | 0 | 0 | 0 | 0 |
| 7 | 0 | 0 | 0 | 0 |
| 9 | 0 | 0 | 0 | 0 |
| 10 | 0 | 0 | 0 | 0 |
| 11 | 0 | 0 | 0 | 0 |
| 13 | 0 | 0 | 0 | 0 |

TABLE 1-continued

| Compounds according to Example No. | leaf surface infested with powdery mildew of wheat in % at mg of active substance/liter of spray liquor | | | |
|---|---|---|---|---|
| | 500 | 250 | 125 | 60 |
| 16 | 0 | 0 | 0 | 0 |
| 21 | 0 | 0 | 0 | 0 |
| 26 | 0 | 0 | 0 | 0 |
| 27 | 0 | 0 | 0 | 0 |
| 30 | 0 | 0 | 0 | 0 |
| 31 | 0 | 0 | 0 | 0 |
| 34 | 0 | 0 | 0 | 0 |
| 41 | 0 | 0 | 0 | 0 |
| 42 | 0 | 0 | 0 | 0 |
| 53 | 0 | 0 | 0 | 0 |
| 59 | 0 | 0 | 0 | 0 |
| 61 | 0 | 0 | 0 | 0 |
| 62 | 0 | 0 | 0 | 0 |
| untreated, infected plants | | 100 | | |

Example 2

Wheat of the type "Jubilar" was treated in the 2-leaf stage with aqueous suspensions of the claimed compound until dripping wet.

After the spray coating had dried on, the plants were inoculated with an aqueous spore suspension of *Puccinia recondita*. The plants were placed for about 16 hours while dripping wet in a climatic chamber at 20° C. and about 100% relative atmospheric humidity. The infected plants were then grown further in a greenhouse at a temperature of 22°–25° C. and 50–70% relative atmospheric humidity.

After an incubation time of about 2 weeks, the fungus sporulated on the entire leaf surface of the untreated control plants, such that an assessment of attack of the experimental plants could be carried out. The degree of attack is indicated in % of attacked leaf surface in comparison to the untreated, infected control plants and is reproduced in Table 2.

TABLE 2

| Compounds according to Example No. | leaf surface attacked with *Puccinia recondita* in % at mg/active substance/liter of spray liquor | | | |
|---|---|---|---|---|
| | 500 | 250 | 125 | 60 |
| 1 | 0 | 0 | 0 | 3 |
| 2 | 0 | 0 | 0 | 0 |
| 4 | 0 | 0 | 0 | 0 |
| 5 | 0 | 0 | 0 | 0 |
| 6 | 0 | 0 | 0 | 0 |
| 7 | 0 | 0 | 0 | 0 |
| 8 | 0 | 0 | 0 | 0 |
| 9 | 0 | 0 | 0 | 0 |
| 10 | 0 | 0 | 0 | 0 |
| 11 | 0 | 0 | 0 | 0 |
| 13 | 0 | 0 | 0 | 0 |
| 15 | 0 | 0 | 0 | 3 |
| 16 | 0 | 0 | 0 | 0 |
| 21 | 0 | 0 | 0 | 0 |
| 26 | 0 | 0 | 0 | 0 |
| 27 | 0 | 0 | 0 | 0 |
| 30 | 0 | 0 | 0 | 0 |
| 31 | 0 | 0 | 0 | 0 |
| 38 | 0 | 0 | 0 | 0 |
| 39 | 0 | 0 | 0 | 0 |
| 41 | 0 | 0 | 0 | 0 |
| 42 | 0 | 0 | 0 | 0 |

TABLE 2-continued

| Compounds according to Example No. | leaf surface attacked with *Puccinia recondita* in % at mg/active substance/liter of spray liquor | | | |
|---|---|---|---|---|
| | 500 | 250 | 125 | 60 |
| 53 | 0 | 0 | 0 | 0 |
| 55 | 0 | 0 | 0 | 0 |
| 59 | 0 | 0 | 0 | 0 |
| 60 | 0 | 0 | 0 | 3 |
| 61 | 0 | 0 | 0 | 0 |
| 62 | 0 | 0 | 0 | 0 |
| untreated, infected plants | | 100 | | |

Example 3

Apple stocks (BM, IX) were uniformly wetted in the 4-leaf stage with the claimed compounds in the application concentrations mentioned in Tab. 3. After the active substance coating had dried on, the plants were heavily infected with conidia of apple scab (*Venturia inaequalis*) and placed dripping wet in a climatic chamber whose temperature was 22° C. and whose relative atmospheric humidity was 100%. After an infection time of 48 hours, the plants were transferred to a greenhouse at 18° C. and a relative atmospheric humidity of 95–100%. After an incubation time of 14 days, the plants were examined for attack with apple scab (*Venturia inaequalis*). Assessment of the attack was carried out in the usual manner according to Augenschein. The degree of attack of the plants with apple scab is expressed in % of attacked leaf surface, relative to untreated, infected plants, and is reproduced in Table 3.

TABLE 3

| Compounds according to Example No. | % scab attack at mg of active substance/liter of spray liquor | | | |
|---|---|---|---|---|
| | 500 | 250 | 125 | 60 |
| 21 | 0 | 0 | 0 | 0 |
| 27 | 0 | 0 | 0 | 0 |
| 62 | 0 | 0 | 0 | 0 |
| 61 | 0 | 0 | 0 | 0 |
| 26 | 0 | 0 | 0 | 0 |
| 11 | 0 | 0 | 0 | 0 |
| 9 | 0 | 0 | 0 | 0 |
| 6 | 0 | 0 | 0 | 0 |
| 5 | 0 | 0 | 0 | 0 |
| untreated, infected plants | | 100 | | |

Example 4

Wheat plants of the type "Jubilar" were treated in the 2-leaf stage with aqueous suspensions of the claimed compounds until dripping wet.

After the spray coating had dried on, the plants were inoculated with an aqueous pycnospore suspension of *Leptosphaeria nodorum* and incubated for several hours at 100% relative atmospheric humidity in a climatic chamber.

Until appearance of symptoms, the plants were grown further in a greenhouse at about 90% relative atmospheric humidity.

The degree of attack is expressed in % of attacked leaf surface in comparison to untreated infected control plants and is reproduced in Table 4.

TABLE 4

| Compounds according to Example No. | leaf surface attacked with Leptosphaeria nodorum in % at mg of active substance/liter of spray liquor | |
|---|---|---|
| | 500 | 250 |
| 4 | 0 | 0 |
| 6 | 0 | 0 |
| 7 | 0 | 0 |
| 8 | 0 | 0 |
| 9 | 0 | 0 |
| 10 | 0 | 0 |
| 13 | 0 | 0 |
| 15 | 0 | 0 |
| 18 | 0 | 0 |
| 20 | 0 | 0 |
| 21 | 0 | 0 |
| 25 | 0 | 0 |
| 27 | 0 | 0 |
| 31 | 0 | 0 |
| 32 | 0 | 0 |
| 34 | 0 | 0 |
| 42 | 0 | 0 |
| 53 | 0 | 0 |
| 55 | 0 | 0 |
| 56 | 0 | 0 |
| 58 | 0 | 0 |
| 62 | 0 | 0 |
| untreated, infected plants | | 100 |

Example 5

Bean plants (Phaseolus v.) heavily infested with bean spider mites (*Tetranychus urticae*, complete population) were sprayed with the aqueous dilution of a wettable powder concentrate which contained 1000 ppm of the respective active substance.

The mortality of the mites was checked after 7 days. 100% mortality was achieved with the compounds according to Examples 3, 4, 6, 7, 9, 10, 11, 13, 15, 21, 26, 27, 30, 32, 34, 39, 42, 53, 56, 58, 60, 61, 62 and 63.

Example 6

Field beans (*Vicia faba*) heavily infested with the black bean aphid (*Aphis fabae*) were sprayed with aqueous dilutions of wettable powder concentrates of 1000 ppm active substance content up to the start of the dripping-off stage. The mortality of the aphids was determined after 3 days. A 100% mortality could be achieved with the compounds according to Examples 3, 4, 5, 6, 8, 9, 10, 11, 13, 15, 21, 26, 27, 30, 31, 32, 35, 38, 39, 41, 42, 53, 56, 58, 61, 62 and 63.

Example 7

To the inside of the lid and the bottom of a petri dish, 1 ml in each case of the formulation to be tested was applied uniformly emulsified in water and, after the coating had dried on, 10 imagines of the housefly (*Musca domestica*) were introduced in each case. After closing the dish, these are kept at room temperature and the mortality of the experimental animals is determined after 3 hours. At 250 ppm (relative to the content of active substance), the preparations 6, 10, 21, 31, 35, 42, 56, 58, 61, 62 and 63 show a good action (100% mortality) against the housefly.

We claim:
1. Substituted 4-aminopyrimidines of the formula I

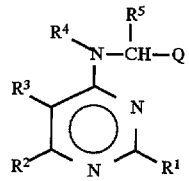

in which

R$^1$ is hydrogen, halogen, (C$_1$–C$_4$)alkyl or (C$_3$–C$_6$) cycloalkyl,

R$^2$ is (C$_1$–C$_4$)alkoxy-(C$_1$–C$_4$)alkyl, or (C$_1$–C$_4$)alkylthio-(C$_1$–C$_4$) alkyl, R$^3$ is (C$_1$–C$_4$)alkoxy, R$^4$ is hydrogen or a radical —C(O)-N-R$^6$R$^7$ in which R$^6$ or R$^7$ are identical or different and are in each case hydrogen, (C$_1$–C$_{14}$) alkyl, phenyl or phenyl-(C$_1$–C$_4$) alkyl, where the abovementioned two phenyl groups are unsubstituted or provided with one or two substituents, it being possible for these substituents in each case to be halogen, (C$_1$–C$_4$)alkyl, (C$_1$–C$_4$) haloalkyl, (C$_1$–C$_4$)alkoxy, (C$_1$–C$_4$) -alkylthio or nitro, or R$^6$ and R$^7$ together with the nitrogen atom to which they are bonded form a saturated or unsaturated 5- or 6-membered ring selected from the group consisting of imidazole, pyrazole, 1,2,4-triazole, thiazole, piperazine, morpholine and thiomorpholine, which can be provided with one of two substituents, it being possible for these substituents in each case to be (C$_1$–C$_4$)alkyl, trifluoromethyl, halogen, (C$_1$–C$_4$) alkoxy, (C$_1$–C$_4$)alkylthio or nitro, R$^5$ is hydrogen, (C$_1$–C$_8$)alkyl or (C$_3$–C$_6$) cycloalkyl, Q has the meaning of Q$^1$ and Q$^1$ is (C$_1$–C$_{15}$)alkyl, optionally substituted by one, two or three halogen atoms, a (C$_1$–C$_{15}$)alkoxy group, a (C$_4$–C$_8$)cycloalkylalkoxy group, a dioxolanyl group, a (C$_1$–C$_4$) alkoxy-(C$_1$–C$_4$)alkoxy group, a hydroxyl group, a methoxycarbonyl group, a (C$_3$–C$_6$)cycloalkyl group, a 2-[2-((C$_1$–C$_4$)alkoxy)ethoxy]ethoxy group, a pyranyloxy group, an imidazol-1-yl group, a triazol-1-yl group, a pyrazol-1-yl group or a group -A-B-R$^8$ in which A is oxygen, sulfur or imino, B is carbonyl, thiocarbonyl or sulfonyl and R$^8$ is (C$_1$–C$_4$) alkyl, (C$_3$–C$_6$) cycloalkyl, (C$_1$–C$_4$) haloalkyl, (C$_1$–C$_4$)alkoxy, a substituted or unsubstituted phenoxy group, a substituted or unsubstituted phenyl group, a substituted or unsubstituted anilino group, a 2,6-dimethylmorpholin-4-yl, 4-methylpiperazin-1-yl, imidazol-1-yl, triazol-1-yl, pyrazol-1-yl group or a mono- or di-(C$_1$–C$_4$) alkylamino group, or Q has the meaning of Q$^2$ and Q$^2$ is a group of the formulae II, II', II'', II''' or II''''

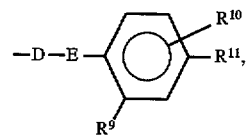

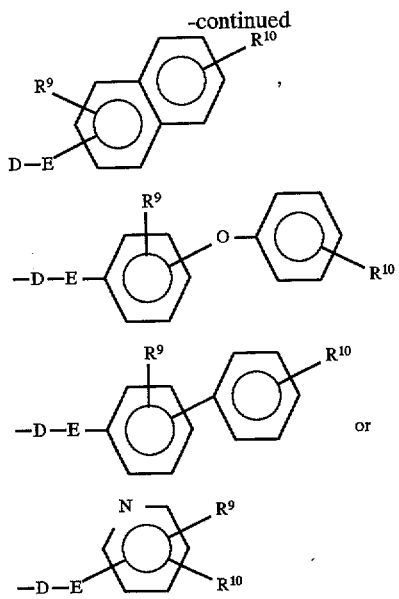

in which

D is a $(C_1-C_6)$alkylene group,

E is a direct bond, oxygen or methyleneoxy, $R^9$ and $R^{10}$ are identical or different and are in each case hydrogen, halogen, $(C_1-C_4)$alkyl, $(C_3-C_6)$ cycloalkyl, $(C_1-C_4)$haloalkyl, $C_3$- or $C_4$-alkenyl, $(C_1-C_4)$alkoxy, $(C_1-C_4)$alkylthio or nitro, $R^{11}$ has the meanings given for $R^9$ and $R^{10}$ and, provided that E is oxygen, $R^{11}$ is a group of the formula $X-Y-(GO)_n-R^{12}$ in which X is a $(C_1-C_8)$alkylene group or a $(C_1-C_4)$alkyleneoxy-$(C_1-C_4)$alkylene group, Y is oxygen, sulfur or an imino group, G is a $(C_1-C_8)$alkylene group or a $(C_1-C_4)$alkyleneoxy-$(C_1-C_4)$alkylene group, n is zero or 1, $R^{12}$ is $(C_1-C_4)$alkyl, $C_3$- or $C_4$-alkenyl, $(C_4-C_6)$ alkadienyl, $C_3$- or $C_4$-alkynyl, phenyl-$(C_1-C_3)$alkyl or a group of the formula $CH_2$—W in which W is a group of the formula $CH=N-OR^{13}$ in which $R^{13}$ is hydrogen, $(C_1-C_4)$alkyl, $C_3$- or $C_4$-alkenyl or phenyl-$(C_1-C_3)$alkyl, Q has the meaning of $Q^3$ $Q^3$ is a group of the formula III

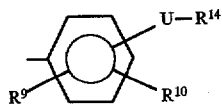

in which $R^9$ and $R^{10}$ have the meanings given above, and

U is a direct bond, oxygen, sulfur, $(C_1-C_3)$alkylene or $(C_1-C_3)$alkyleneoxy, $R^{14}$ is phenyl or a heterocycle selected from the group consisting of pyridine, pyrimidine, quinoxaline, pyrazine benzoxazole, benzothiazole and quinoline, it being possible for each of the abovementioned two radicals to be unsubstituted or provided with one or two substituents, where these substituents are identical or different and are in each case halogen, $(C_1-C_4)$alkyl, $(C_1-C_4)$ haloalkyl, nitro, $(C_1-C_4)$alkoxy, $(C_1-C_4)$ alkylthio, $(C_1-C_4)$alkoxy-$(C_1-C_4)$alkyl, phenyl, phenoxy, halophenoxy or $(C_1-C_4)$ alkylphenoxy, provided that U is oxygen, $R^{14}$ is $(C_5-C_{10})$alkyl, allyl, geranyl, farnesyl, $(C_1-C_4)$ haloalkyl, $(C_3-C_6)$ cycloalkylmethyl, an ethyl group which is substituted in the 2-position by $(C_1-C_4)$alkoxy, $(C_1-C_4)$ alkoxy-$(C_1-C_4)$alkyl, $(C_1-C_4)$alkylthio, $(C_1-C_4)$alkylsulfonyl or a phenoxy group which can optionally be substituted by one or two $(C_1-C_4)$alkyl groups, or glycidyl, acetonyl, halophenoxyethyldioxolanyl, 2,2-diethoxyethyl, 1-ethoxycarbonylmethyl, trimethylsilylmethyl, 1-pyridylethyl or a $(C_1-C_4)$alkyl group which is substituted by a $(C_1-C_4)$alkoxyimino or a benzyloxyimino group, a group of formula IV

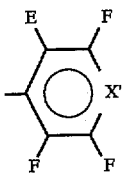

in which

X' is nitrogen or a group $CR^{15}$ in which $R^{15}$ is hydrogen, halogen, $(C_1-C_4)$alkyl, $(C_1-C_4)$ haloalkyl, $(C_1-C_4)$alkanoyl, nitro, cyano or 1,3-dioxolan-2-yl, and their salts and stereoisomers.

2. A compound as claimed in claim 1, wherein, in formula I, $R^1$ is hydrogen, methyl or halogen, $R^2$ is methoxymethyl, $R^3$ is $(C_1-C_4)$alkoxy.

3. A compound as claimed in claim 1, wherein, in formula I $R^2$ is methoxymethyl, $R^3$ is $(C_1-C_4)$alkoxy, $R^4$ is hydrogen, $R^5$ is hydrogen, $(C_1-C_4)$alkyl or cyclopropyl, Q has the meaning of $Q^1$ and $Q^1$ is $(C_1-C_{15})$alkyl, optionally substituted by one, two or three halogen atoms, a $(C_1-C_{15})$alkoxy group, a $(C_4-C_8)$cycloalkylalkoxy group, a dioxolanyl group, a $(C_1-C_4)$alkoxy-$(C_1-C_4)$alkoxy group, a hydroxyl group, a methoxycarbonyl group, a $(C_3-C_6)$ cycloalkyl group, a 2-[2-(($C_1-C_4$)alkoxy)ethoxy]ethoxy group, a pyranyloxy group, an imidazol-1-yl group, a triazol-1-yl group, a pyrazol-1-yl group or a group -A-B-$R^8$ in which A is oxygen, sulfur or imino, B is carbonyl, thiocarbonyl or sulfonyl and $R^8$ is $(C_1-C_4)$alkyl, $(C_3-C_6)$cycloalkyl, $(C_1-C_4)$haloalkyl, $(C_1-C_4)$alkoxy, a substituted or unsubstituted phenoxy group, a substituted or unsubstituted phenyl group, a substituted or unsubstituted anilino group, a 2,6-dimethylmorpholin-4-yl, 4-methylpiperazin-1-yl, imidazol-1-yl, triazol-1-yl, pyrazol-1-yl group or a mono- or di-$(C_1-C_4)$ alkylamino group.

4. A compound as claimed in claim 1, wherein, in formula I, $R^2$ is methoxymethyl, $R^3$ is $(C_1-C_4)$alkoxy, $R^4$ is hydrogen, $R^5$ is hydrogen, $(C_1-C_4)$alkyl or cyclopropyl, Q has the meaning of $Q^2$ and $Q^2$ is a group of the formulae II, II', II'', II''' or II'''' in which D is a $(C_1-C_6)$alkylene group, E is a direct bond, oxygen or methyleneoxy, $R^9$ and $R^{10}$ are identical or different and are in each case hydrogen, halogen, $(C_1-C_4)$alkyl, $(C_3-C_5)$cycloalkyl, $(C_1-C_4)$haloalkyl, $C_3$- or $C_4$-alkenyl, $(C_1-C_4)$alkoxy, $(C_1-C_4)$alkylthio or nitro, $R^{11}$ has the meanings given for $R^9$ and $R^{10}$ and, provided that E is oxygen, $R^{11}$ is a group of the formula X-Y-(GO)$_n$-$R^{12}$ in which X is a $(C_1-C_8)$alkylene group or a $(C_1-C_8)$alkylene group having a $(C_1-C_4)$alkoxy substituent, Y is oxygen, sulfur or an imino group, G is a $(C_1-C_8)$alkylene group or a $(C_1-C_4)$alkyleneoxy-$(C_1-C_4)$alkylene group, n is zero or 1, $R^{12}$ is $(C_1-C_4)$alkyl, $C_3$- or $C_4$-alkenyl, $(C_4-C_6)$alkadienyl, $C_3$- or $C_4$-alkynyl, phenyl-$(C_1-C_3)$alkyl or a group of the formula $CH_2$—W in which W is a group of the formula $CH=N-OR^{13}$ in which $R^{13}$ is hydrogen, $(C_1-C_4)$ alkyl, $C_3$- or $C_4$-alkenyl or phenyl-$(C_1-C_3)$alkyl.

5. A compound as claimed in claim 1, wherein, in formula I, $R^2$ is methoxymethyl, $R^3$ is $(C_1-C_4)$alkoxy, $R^4$ is hydrogen, $R^5$ is hydrogen, $(C_1-C_4)$alkyl or cyclopropyl, Q has the meaning of $Q^3$ and $Q^3$ is a group of the formula III in which $R^9$ and $R^{10}$ have the meanings mentioned, U is a direct bond, oxygen, sulfur, $(C_1-C_3)$alkylene or $(C_1-C_3)$ alkyleneoxy, and $R^{14}$ is phenyl or a heterocycle, it being possible for each of the abovementioned two radicals to be unsubstituted or provided with one or two substituents, where these substituents are identical or different and are in each case halogen, $(C_1-C_4)$alkyl, $(C_1-C_4)$haloalkyl, nitro, $(C_1-C_4)$alkoxy, $(C_1-C_4)$alkylthio, $(C_1-C_4)$alkoxy-$(C_1-C_4)$alkyl, phenyl, phenoxy, halophenoxy or $(C_1-C_4)$ alkylphenoxy, or provided that U is oxygen, $R^{14}$ is $(C_5-C_{10})$alkyl, allyl, geranyl, farnesyl, $(C_1-C_4)$haloalkyl, $(C_3-C_6)$cycloalkylmethyl, an ethyl group which is substituted in the 2-position by $(C_1-C_4)$ alkoxy, $(C_1-C_4)$alkoxy-$(C_1-C_4)$alkyl, $(C_1-C_4)$alkylthio, $(C_1-C_4)$alkylsulfonyl or a phenoxy group which can optionally be substituted by one or two $(C_1-C_4)$alkyl groups, or glycidyl, acetonyl, halophenoxymethyldioxolanyl, 2,2-diethoxyethyl, 1-ethoxycarbonylmethyl, trimethylsilylmethyl, 1-pyridylethyl or a $(C_1-C_4)$alkyl group which is substituted by a $(C_1-C_4)$alkoxyimino or a benzyloxyimino group, or group of the formula IV in which X' is nitrogen or a group $CR^{15}$ in which $R^{15}$ is hydrogen, halogen, $(C_1-C_4)$alkyl, $(C_1-C_4)$haloalkyl, $(C_1-C_4)$ alkanoyl, nitro, cyano or 1,3-dioxolan-2-yl.

6. A compound as claimed in claim 1, wherein, in formula I, $R^2$ is methoxymethyl, is methoxy or ethoxy, $R^4$ is hydrogen.

7. A compound as claimed in claim 1, wherein, in formula I, $R^2$ is methoxymethyl, $R^3$ is methoxy or ethoxy, $R^4$ is hydrogen, Q has the meaning of $Q^1$ and $Q^1$ is $(C_1-C_{15})$alkyl, optionally substituted by one, two or three halogen atoms, a $(C_1-C_{15})$alkoxy group, a $(C_4-C_8)$cycloalkylalkoxy group, a dioxolanyl group, a $(C_1-C_4)$alkoxy-$(C_1-C_4)$alkoxy group, a hydroxyl group, a methoxycarbonyl group, a $(C_3-C_6)$cycloalkyl group, a 2-[2-$((C_1-C_4)$alkoxy)ethoxy]ethoxy group, a pyranyloxy group, an imidazol-1-yl group, a triazol-1-yl group, a pyrazol-1-yl group or a group -A-B-$R^8$ in which A is oxygen, sulfur or imino, B is carbonyl, thiocarbonyl or sulfonyl and $R^8$ is $(C_1-C_4)$alkyl, $(C_3-C_6)$cycloalkyl, $(C_1-C_4)$haloalkyl, $(C_1-C_4)$alkoxy, a substituted or unsubstituted phenoxy group, a substituted or unsubstituted phenyl group, a substituted or unsubstituted anilino group, a 2,6-dimethylmorpholin-4-yl, 4-methylpiperazin-1-yl, imidazol-1-yl, triazol-1-yl, pyrazol-1-yl group or mono- or di-$(C_1-C_4)$ alkylamino group.

8. A compound as claimed in claim 1, wherein in formula I, $R^2$ is methoxymethyl, $R^3$ is methoxy or ethoxy, $R^4$ is hydrogen, Q has the meaning of $Q^2$ and $Q^2$ is a group of the formulae II, II', II", II''' or II'''' in which D is a $(C_1-C_6)$alkylene group, E is a direct bond, oxygen or methyleneoxy, $R^9$ and $R^{10}$ are identical or different and are in each case hydrogen, halogen, $(C_1-C_4)$alkyl, $(C_3-C_6)$cycloalkyl, $(C_1-C_4)$haloalkyl, $C_3$- or $C_4$-alkenyl, $(C_1-C_4)$alkoxy, $(C_1-C_4)$alkylthio or nitro, $R^{11}$ has the meanings given for $R^9$ and $R^{10}$ and, provided that E is oxygen, $R^{11}$ is a group of the formula X-Y-(GO)$_n$-$R^{12}$ in which X is a $(C_1-C_8)$ alkylene group or a $(C_1-C_8)$alkylene group having a $(C_1-C_4)$alkoxy substituent, Y is oxygen, sulfur or an imino group, G is a $(C_1-C_8)$alkylene group or a $(C_1-C_8)$alkadienyl, $(C_1-C_4)$alkylene group, n is zero or 1, $R^{12}$ is $(C_1-C_4)$alkyl, $C_3$- or $C_4$-alkenyl, $(C_4-C_6)$alkadienyl, $C_3$- or $C_4$-alkynyl, phenyl-$(C_1-C_3)$alkyl or a group of the formula $CH_2$—W in which W is a group of the formula $CH=N-OR^{13}$ in which $R^{13}$ is hydrogen, $(C_1-C_4)$alkyl, $C_3$- or $C_4$-alkenyl or phenyl-$(C_1-C_3)$alkyl.

9. A compound as claimed in claim 1, wherein in formula I, $R^2$ is methoxymethyl, $R^3$ is methoxy or ethoxy, $R^4$ is hydrogen, Q has the meaning of $Q^3$ and $Q^3$ is a group of the formula III in which $R^9$ and $R^{10}$ have the meanings mentioned, U is a direct bond, oxygen, sulfur, $(C_1-C_3)$alkylene or $(C_1-C_3)$alkyleneoxy, and $R^{14}$ is phenyl or a heterocycle, it being possible for each of the abovementioned two radicals to be unsubstituted or provided with one or two substituents, where these substituents are identical or different and are in each case halogen, $(C_1-C_4)$alkyl, $(C_1-C_4)$haloalkyl, $(C_1-C_4)$ alkoxy, nitro, $(C_1-C_4)$alkylthio, $(C_1-C_4)$ alkoxy-$(C_1-C_4)$alkyl, phenyl, phenoxy, halophenoxy or $(C_1-C_4)$alkylphenoxy, or provided that U is oxygen, $R^{14}$ is $(C_5-C_{10})$alkyl, allyl, geranyl, farnesyl, $(C_1-C_4)$ haloalkyl, $(C_3-C_6)$cycloalkylmethyl, an ethyl group which is substituted in the 2-position by $(C_1-C_4)$ alkoxy, $(C_1-C_4)$alkoxy-$(C_1-C_4)$alkyl, $(C_1-C_4)$ alkylthio, $(C_1-C_4)$alkylsulfonyl or a phenoxy group which can optionally be substituted by one or two $(C_1-C_4)$alkyl groups, or glycidyl, acetonyl, halophenoxymethyldioxolanyl, 2,2-diethoxyethyl, 1-ethoxycarbonylmethyl, trimethylsilylmethyl, 1-pyridylethyl or a $(C_1-C_4)$alkyl group which is substituted by a $(C_1-C_4)$alkoxyimino or a benzyloxyimino group and a group of the formula IV in which X' is nitrogen or a group $CR^{15}$ in which $R^{15}$ is hydrogen, halogen, $(C_1-C_4)$alkyl, $(C_1-C_4)$ haloalkyl; $(C_1-C_4)$ alkanoyl, nitro, cyano or 1,3-dioxolan-2-yl .

10. A compound as claimed in claim 1, wherein in formula I, $R^1$ is hydrogen, $R^2$ is methoxymethyl, $R^3$ is methoxy and $R^4$ is hydrogen.

11. A compound as claimed in claim 10, wherein in formula I, $R^5$ is hydrogen, methyl, ethyl or cyclopropyl.

12. A compound as claimed in claim 10, wherein in formula I, $R^2$ is methoxymethyl, $R^5$ is hydrogen, methyl or cyclopropyl, Q has the meaning of $Q^1$ and $Q^1$ is $(C_3-C_{13})$alkyl.

13. A compound as claimed in claim 10, wherein, in formula I, $R^5$ is hydrogen, methyl or cyclopropyl, Q has the meaning of $Q^2$ and $Q^2$ is a group of the formulae II, II', II'', II''' or II'''' which D is a $(C_1-C_2)$alkylene group, E is a direct bond or oxygen, $R^9$ and $R^{10}$ are identical or different and are in each case hydrogen, halogen, $(C_1-C_4)$alkyl, $(C_3-C_6)$cycloalkyl, $(C_1-C_4)$haloalkyl, $(C_1-C_4)$alkoxy, $R^{11}$ has the meanings given for $R^9$ and $R^{10}$ and, provided that E is oxygen, $R^{11}$ is a group of the formula X-Y(GO)$_n$-$R^{12}$ in which, X is a $(C_1-C_8)$alkylene group, Y is oxygen, G is an ethylene group, n is zero or 1 and $R^{12}$ is $(C_1-C_4)$alkyl.

14. A compound as claimed in claim 10, wherein, in formula I,

Q has the meaning of $Q^3$ and $Q^3$ is a group of the formula III in which $R^9$ and $R^{10}$ have the meanings mentioned, U is oxygen, and $R^{14}$ is phenyl or a heterocycle, it being possible for each of the abovementioned two radicals to be unsubstituted or provided with one or two substituents, where these substituents are identical or different and are in each case halogen, $(C_1-C_4)$alkyl, $(C_1-C_4)$haloalkyl, $(C_1-C_4)$ alkoxy, nitro, $(C_1-C_4)$alkylthio, $(C_1-C_4)$alkoxy-$(C_1-C_4)$alkyl, phenyl, phenoxy, halophenoxy or $(C_1-C_4)$alkylphenoxy, X' is nitrogen or a group of the formula CF.

15. An insecticidal or acaricidal agent, comprising an insecticidally or acaricidally active amount of a compound of the formula I as claimed in claim 1 and the customary additives and/or auxiliaries.

16. A fungicidal agent, comprising a fungicidally active amount of a compound of the formula I as claimed in claim 1 and the customary additives and/or auxiliaries.

17. A nematocidal agent, comprising a nematocidally active amount of a compound of the formula I as claimed in claim 1, and the customary additives and/or auxiliaries.

18. A method of controlling insect pests and acarids, which comprises applying an effective amount of a compound of the formula I as claimed in claim 1 to these insect pests or acarids or the plants, areas or substrates attacked by them.

19. A method of controlling fungal pests, which comprises applying an effective amount of a compound of the formula I as claimed in claim 1 to these fungal pests or the plants, areas or substrates attacked by them.

20. A method of controlling nematodes, which comprises applying an effective amount of a compound of the formula I as claimed in claim 1 to these nematodes or to the plants, areas or substrates attacked by them.

* * * * *